United States Patent
Allen et al.

(10) Patent No.: US 10,360,301 B2
(45) Date of Patent: Jul. 23, 2019

(54) PERSONALIZED APPROACH TO HANDLING HYPOTHETICALS IN TEXT

(71) Applicant: International Business Machines Corporation, Armonk, NY (US)

(72) Inventors: Corville O. Allen, Morrisville, NC (US); Roberto DeLima, Apex, NC (US); Aysu Ezen Can, Cary, NC (US); Robert C. Sizemore, Fuquay-Varina, NC (US)

(73) Assignee: International Business Machines Corporation, Armonk, NY (US)

( * ) Notice: Subject to any disclaimer, the term of this patent is extended or adjusted under 35 U.S.C. 154(b) by 306 days.

(21) Appl. No.: 15/289,224

(22) Filed: Oct. 10, 2016

(65) Prior Publication Data
US 2018/0101598 A1    Apr. 12, 2018

(51) Int. Cl.
*G06F 17/27* (2006.01)
*G16H 10/00* (2018.01)

(52) U.S. Cl.
CPC ........ *G06F 17/2785* (2013.01); *G06F 17/274* (2013.01); *G06F 17/2715* (2013.01);
(Continued)

(58) Field of Classification Search
CPC ............. G06F 17/2785; G06F 17/2775; G06F 17/2715; G06F 17/274; G06F 17/2735; G06F 17/2755; G16H 10/00
(Continued)

(56) References Cited

U.S. PATENT DOCUMENTS 6,108,620 A * 8/2000 Richardson ........... G06F 17/271
704/10
6,154,739 A 11/2000 Wrobel
(Continued)

FOREIGN PATENT DOCUMENTS

WO    WO-2013191662 A1 * 12/2013 ........... G06F 17/274

OTHER PUBLICATIONS

Kang et al., "A Comparison of Classifiers for Detecting Hedges", T.-h. Kim et al. (Eds.): UNESST 2011, CCIS 264, pp. 251-257, 2011. (Year: 2011).*

(Continued)

*Primary Examiner* — Phuong Thao Cao
(74) *Attorney, Agent, or Firm* — Stephen J. Walder, Jr.; Reza Sarbakhsh

(57) ABSTRACT

Mechanisms receive natural language content and analyze the natural language content to generate a parse tree data structure. The mechanisms process the parse tree data structure to identify one or more instances of candidate hypothetical spans in the natural language content. Hypothetical spans are terms or phrases indicative of a hypothetical statement. The mechanisms calculate, for each candidate hypothetical span, a confidence score value indicative of a confidence that the candidate hypothetical span is an actual hypothetical span based on a personalized hypothetical dictionary data structure associated with a source of the natural language content. The mechanisms perform an operation based on the natural language content. The operation is performed with portions of the natural language content corresponding to the one or more identified instances of actual hypothetical spans being given different relative weights within portions of the natural language content than other portions of the natural language content.

19 Claims, 8 Drawing Sheets

(52) U.S. Cl.
CPC ...... *G06F 17/2735* (2013.01); *G06F 17/2755* (2013.01); *G06F 17/2775* (2013.01); *G16H 10/00* (2018.01)

(58) Field of Classification Search
USPC ........................................................ 707/728
See application file for complete search history.

(56) References Cited

U.S. PATENT DOCUMENTS

| | | | |
|---|---|---|---|
| 6,236,959 B1* | 5/2001 | Weise | G06F 17/2705 704/9 |
| 6,920,420 B2 | 7/2005 | Lin | |
| 7,324,936 B2 | 1/2008 | Saldanha et al. | |
| 7,937,386 B2 | 5/2011 | Barrett et al. | |
| 8,275,803 B2 | 9/2012 | Brown et al. | |
| 8,880,537 B2 | 11/2014 | Fuchs | |
| 9,152,623 B2 | 10/2015 | Wroczynski et al. | |
| 9,275,341 B2 | 3/2016 | Cruse et al. | |
| 9,292,487 B1* | 3/2016 | Weber | G06F 17/27 |
| 9,703,861 B2 | 7/2017 | Brown et al. | |
| 2002/0042711 A1 | 4/2002 | Lin | |
| 2003/0120479 A1* | 6/2003 | Parkinson | G06F 17/271 704/4 |
| 2003/0212544 A1* | 11/2003 | Acero | G06F 17/241 704/9 |
| 2003/0216905 A1* | 11/2003 | Chelba | G06F 17/271 704/9 |
| 2004/0034525 A1* | 2/2004 | Pentheroudakis | G06F 17/2705 704/9 |
| 2004/0088210 A1* | 5/2004 | Tsyganskiy | G06Q 30/02 705/7.33 |
| 2004/0220809 A1* | 11/2004 | Wang | G06F 17/2705 704/257 |
| 2005/0033711 A1* | 2/2005 | Horvitz | G06F 17/30684 706/50 |
| 2005/0055209 A1* | 3/2005 | Epstein | G10L 15/1815 704/255 |
| 2005/0120009 A1* | 6/2005 | Aker | G06F 17/30914 |
| 2006/0004683 A1* | 1/2006 | Talbot | G06K 9/6292 706/59 |
| 2007/0016862 A1* | 1/2007 | Kuzmin | G06F 3/0236 715/700 |
| 2007/0282590 A1* | 12/2007 | Suzuki | G06F 17/274 704/2 |
| 2008/0071520 A1* | 3/2008 | Sanford | G06F 17/271 704/9 |
| 2008/0270120 A1 | 10/2008 | Pestian et al. | |
| 2009/0287678 A1 | 11/2009 | Brown et al. | |
| 2010/0037212 A1* | 2/2010 | Meijer | G06F 8/427 717/142 |
| 2010/0169359 A1 | 7/2010 | Barrett et al. | |
| 2010/0280821 A1* | 11/2010 | Tiitola | G06F 17/276 704/200 |
| 2011/0010163 A1* | 1/2011 | Jansen | G06F 17/271 704/9 |
| 2011/0066587 A1 | 3/2011 | Ferrucci et al. | |
| 2011/0125734 A1 | 5/2011 | Duboue et al. | |
| 2013/0007055 A1 | 1/2013 | Brown et al. | |
| 2013/0018652 A1 | 1/2013 | Ferrucci et al. | |
| 2013/0021346 A1* | 1/2013 | Terman | G09B 5/08 345/467 |
| 2013/0030793 A1 | 1/2013 | Cal et al. | |
| 2013/0066886 A1 | 3/2013 | Bagchi et al. | |
| 2013/0231916 A1* | 9/2013 | Huerta | G06F 17/2836 704/5 |
| 2013/0232098 A1* | 9/2013 | Tateishi | G06F 17/2785 706/46 |
| 2014/0047315 A1 | 2/2014 | Williams | |
| 2014/0195462 A1* | 7/2014 | Rajaram | G06N 5/00 706/11 |
| 2014/0244524 A1* | 8/2014 | Brestoff | G06Q 50/18 705/311 |
| 2014/0280256 A1* | 9/2014 | Wolfram | G06F 17/30943 707/755 |
| 2014/0343925 A1 | 11/2014 | Mankovich et al. | |
| 2015/0006528 A1* | 1/2015 | Rao | G06F 17/30705 707/730 |
| 2015/0057991 A1 | 2/2015 | Mesheryakov et al. | |
| 2015/0278195 A1* | 10/2015 | Yang | G06F 17/2785 704/9 |
| 2015/0370778 A1* | 12/2015 | Tremblay | G06F 17/2705 704/9 |
| 2016/0062604 A1* | 3/2016 | Kraljic | G06F 3/0482 715/771 |
| 2016/0098387 A1* | 4/2016 | Bruno | G06F 17/2785 704/9 |
| 2016/0098389 A1* | 4/2016 | Bruno | G06F 17/2705 704/9 |
| 2016/0098394 A1* | 4/2016 | Bruno | G06F 17/271 704/9 |
| 2016/0151918 A1* | 6/2016 | Stoyanchev | G06F 17/2785 700/246 |
| 2016/0188570 A1* | 6/2016 | Lobez Comeras | G06F 17/28 704/9 |
| 2018/0075011 A1* | 3/2018 | Allen | G06F 17/2735 |
| 2018/0101598 A1* | 4/2018 | Allen | G06F 17/2715 |

OTHER PUBLICATIONS

Kilicoglu et al., "Recognizing Speculative Language in Biomedical Research Articles: A Linguistically Motivated Perspective", BioNLP 2008: Current Trends in Biomedical Natural Language Processing, pp. 46-53, Columbus, Ohio, USA, Jun. 2008. (Year: 2008).*

Light et al., "The Language of Bioscience: Facts, Speculations, and Statements in Between", HLT-NAACL 2004 Workshop: Biolink 2004, Linking Biological Literature, Ontologies and Databases, pp. 17-24. (Year: 2004).*

Malhotra et al., "'HypothesisFinder:' A Strategy for the Detection of Speculative Statements in Scientific Text", PLOS Computational Biology, Jul. 2013, vol. 9, Issue 7, pp. 1-10. (Year: 2013).*

Medlock et al., "Weakly Supervised Learning for Hedge Classification in Scientific Literature", In Proceedings of the 45th Annual Meeting of the Association of Computational Linguistics, pp. 992-999, Prague, Czech Republic, Jun. 2007. (Year: 2007).*

Moncecchi G., "Recognizing Speculative Language in Research Text", Artificial Intelligence lcs.All, Universite de Nanterre—Paris X, Universidad de la Republica—Proyecto de Apoyo a las Ciencias Basicas, 2013, English, 160 pages. (Year: 2013).*

Rei M., "Minimally Supervised Dependency-Based Methods for Natural Language Processing", Technical Report, No. 840, University of Cambridge, Computer Laboratory, Sep. 2013, 169 pages. (Year: 2013).*

Vlachos et al., "Detecting Speculative Language Using Syntactic Dependencies and Logistic Regression", in Proceedings of the Fourteenth Conference on Computational Natural Language Learning: Shared Task, pp. 18-25, Uppsala, Sweden, Jul. 15-16, 2010. (Year: 2010).*

Cruz Diaz et al., "A Machine-Learning Approach to Negation and Speculation Detection in Clinical Texts", Journal of the American Society for Information Science and Technology, 63(7): pp. 1398-1410, 2012. (Year: 2012).*

Moncecchi et al., "Improving Speculative Language Detection Using Linguistic Knowledge", in Proceedings of the ACL-2012 Workshop on Extra-Propositional Aspects of Meaning in Computational Linguistics (ExProM-2012), pp. 37-46, Jeju, Republic of Korea, Jul. 13, 2012. (Year: 2012).*

Morante et al., "Modality and Negation: An Introduction to the Special Issue", Computational Linguistics, vol. 38, Issue 2, Jun. 2012, pp. 223-260. (Year: 2012).*

Yang et al., "Speculative Requirements: Automatic Detection of Uncertainty in Natural Language Requirements", in Proceedings of the 2012 20th IEEE International Requirements Engineering Conference (RE 2012), Sep. 24-28, 2012, pp. 11-20. (Year: 2012 ).*

Bruno, Nicholas V.et al., "Natural Language Processing Utilizing Logical Tree Structures", filed Oct. 6, 2014, U.S. Appl. No. 14/506,855.

(56) References Cited

OTHER PUBLICATIONS

List of IBM Patents or Patent Applications Treated as Related, Feb. 24, 2017, 2 pages.
Aronow, David B. et al., "Ad Hoc Classification of Radiology Reports", J. of the American Medical Informatics Assoc., vol. 6 No. 5, Sep./Oct. 1999, pp. 393-411.
Chapman, Wendy W. et al., "ConText: An Algorithm for Identifying Contextual Features from Clinical Text", Association for Computational Linguistics, BioNLP 2007: Biological, translational, and clinical language processing, Prague, Jun. 2007, pp. 81-88.
Dalianis, Hercules et al., "Creating and Evaluating a Consensus for Negated and Speculative Words in a Swedish Clinical Corpus", Proceedings of the Workshop on Negation and Speculation in Natural Language Processing, Uppsala, Sweden, Jul. 2010, pp. 5-13.
Descles, Julien et al., "Automatic annotation of speculation in biomedical texts: new perspectives and large-scale evaluation", Proceedings of the Workshop on Negation and Speculation in Natural Language Processing, Uppsala, Sweden, Jul. 2010, pp. 32-40.
Dimarco, C. et al., "The Development of a Natural Language Generation System for Personalized e-Health Information", University of Waterloo, Jan. 2007, 5 pages.
Goldstein, Ira et al., "Does Negation Really Matter?", Proceedings of the Workshop on Negation and Speculation in Natural Language Processing, Uppsala, Sweden, Jul. 2010, pp. 23-27.
Henriksson, Aron et al., "Levels of Certainty in Knowledge-Intensive Corpora: an Initial Annotation Study", Proceedings of the Workshop on Negation and Speculation in Natural Language Processing, Uppsala, Sweden, Jul. 2010, pp. 41-45.
High, Rob, "The Era of Cognitive Systems: An Inside Look at IBM Watson and How it Works", IBM Corporation, Redbooks, Dec. 12, 2012, 16 pages.
Joshi, Yateendra, "Scientific writing: Difference between "to reveal," "to show," and "to indicate"", Editage Insights, http://www.editage.com/insights/scientific-writing-difference-between-to-reveal-to-show-and-to-indicate, Jan. 31, 2014, 5 pages.
Kilicoglu, Halil et al., "Recognizing speculative language in biomedical research articles: a linguistically motivated perspective", BMC Bioinformatics 2008 9 (Suppl 11):S10, Nov. 19, 2008, 10 pages.
Liakata, Maria, "Zones of conceptualisation in scientific papers: a window to negative and speculative statements", Proceedings of the Workshop on Negation and Speculation in Natural Language Processing, Uppsala, Sweden, Jul. 2010, pp. 1-4.
Malhotra, Ashutosh et al., "HypothesisFinder: A Strategy for the Detection of Speculative Statements in Scientific Text", PLOS Computational Biology, vol. 9, Issue 7, Jul. 2013, 10 pages.
McCord, M.C. et al., "Deep parsing in Watson", IBM J, Res. & Dev. vol. 56 No. 3/4 Paper 3, May/Jul. 2012, pp. 3:1-3:15.
Velupillai, Sumithra, "Towards a Better Understanding of Uncertainties and Speculations in Swedish Clinical Text—Analysis of an Initial Annotation Trial", Proceedings of the Workshop on Negation and Speculation in Natural Language Processing, Uppsala, Sweden, Jul. 2010, pp. 14-22.
Vincze, Veronika, "Speculation and negation annotation in natural language texts: what the case of BioScope might (not) reveal", Proceedings of the Workshop on Negation and Speculation in Natural Language Processing, Uppsala, Sweden, Jul. 2010, pp. 28-31.
Vlachos, Andreas et ai., "Detecting Speculative Language Using Syntactic Dependencies and Logistic Regression", Proceedings of the Fourteenth Conference on Computational Natural Language Learning: Shared Task, Jul. 15-16, 2010, pp. 18-25.
Yang, Hui et al, "Speculative Requirements: Automatic Detection of Uncertainty in Natural Language Requirements", Accessed from the Internet on May 4, 2016, http://oro.open.ac.uk/34479/1/_penelope_MCSUsers_Staff_hy237_hy237_Research_Research_Paper_Unpublished_Assertion_RE'12_Camera_ready_re12rnain-p027-yang-10688-submitted.pdf, 10 pages.
Yuan, Michael J., "Watson and healthcare, How natural language processing and semantic search could revolutionize clinical decision support", IBM developerWorks, IBM Corporation, Apr. 12, 2011, 14 pages.
Boon, Jia-Shen et al., "Distributed Representation of Sentences for Speculative Language Recognition in Biomedical Articles", Accessed from the Internet, https://www.semanticscholar.org/paper/Distributed-Representation-of-Sentences-for-Specul-Boon-Gowrisankar/87aadd1744a59d61a13be6364772b8690de38550, Fall 2014, 11 pages.
Goldin, Ilya M. et al., "Learning to Detect Negation with 'Not' in Medical Texts", Proceedings Workshop on Text Analysis and Search for Bioinformatics, The 26th ACM/SIGIR International Symposium on Information Retrieval, Jul. 2003, 7 pages.
Li, Junhui et al., "Learning the Scope of Negation via Shallow Semantic Parsing", Proceedings of the 23rd International Conference on Computation Linguistics (Coling 2010), Beijing, Aug. 2010, pp. 671-679.
Szarvas, Gyorgy et al., "Cross-Genre and Cross-Domain Detection of Semantic Uncertainty", Association for Computational Linguistics 38.2, Jun. 2012, 335-367.
Vincze, Veronika et al., "The BioScope corpus: biomedical texts annotated for uncertainty, negation and their scopes", BMC Bioinformatics, 9.S11, Nov. 2008, 9 pages.

\* cited by examiner

PERSONALIZED APPROACH TO HANDLING HYPOTHETICALS IN TEXT

BACKGROUND

The present application relates generally to an improved data processing apparatus and method and more specifically to mechanisms for providing a personalized approach to handling hypothetical statements in texts such as medical text, judicial statements, and other corpora of textual documents.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain, vomiting, and the like.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions which are executed by the at least one processor and specifically configure the processor to perform the method. The method comprises receiving, by the data processing system, natural language content and analyzing, by the data processing system, the natural language content to generate a parse tree data structure. The method further comprises processing, by the data processing system, the parse tree data structure to identify one or more instances of candidate hypothetical spans in the natural language content. Hypothetical spans are terms or phrases indicative of a hypothetical statement. The method also comprises calculating, by the data processing system, for each candidate hypothetical span, a confidence score value indicative of a confidence that the candidate hypothetical span is an actual hypothetical span based on a personalized hypothetical dictionary data structure associated with a source of the natural language content. In addition, the method comprises performing, by the data processing system, an operation based on the natural language content. The operation is performed with portions of the natural language content corresponding to the one or more identified instances of actual hypothetical spans being given different relative weights within portions of the natural language content than other portions of the natural language content.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
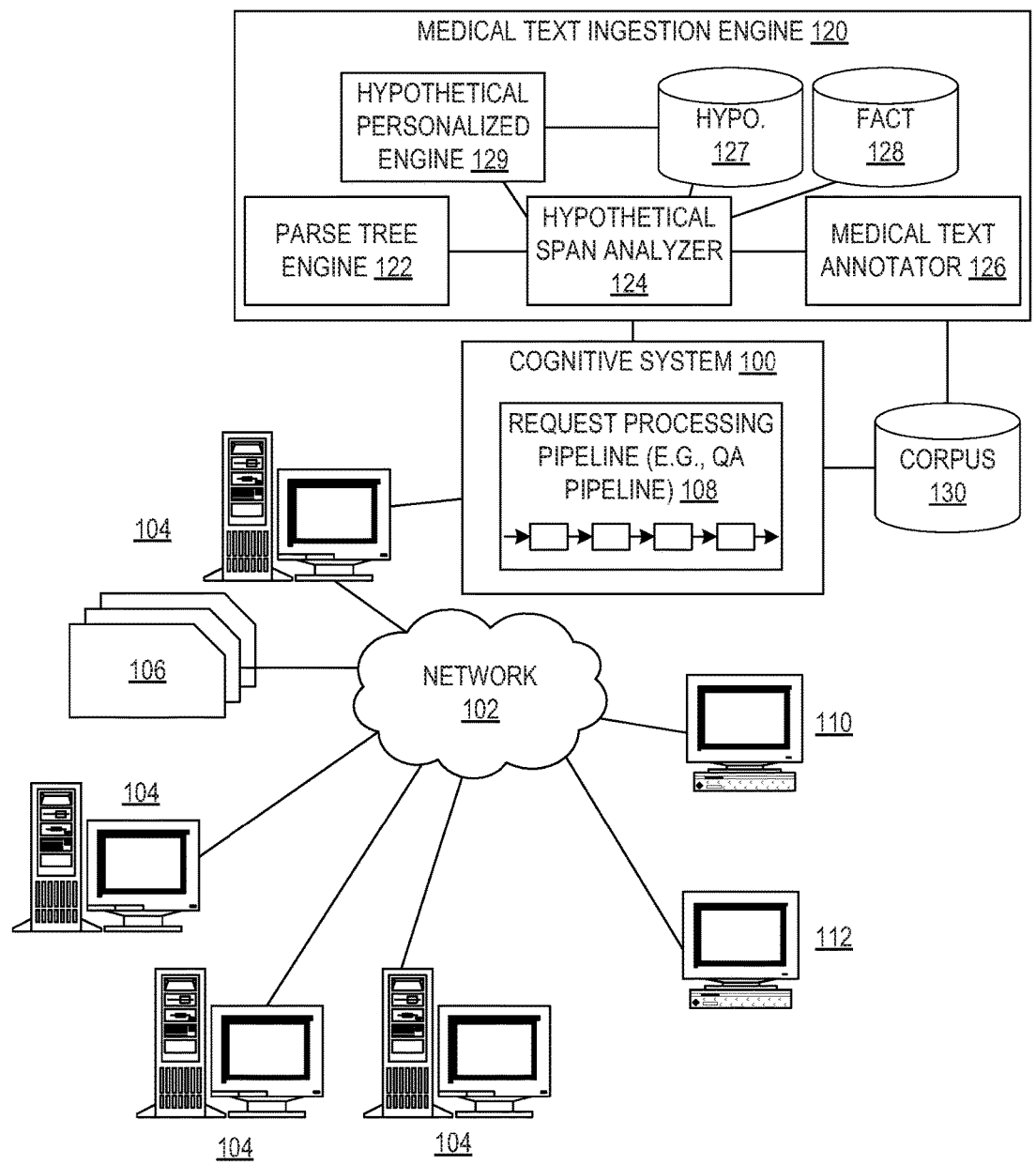
FIG. 1 depicts a schematic diagram of one illustrative embodiment of a cognitive healthcare system in a computer network.

When performing natural language processing of portions of text, such as medical texts, judicial texts, and the like, it is often important to be able to distinguish portions of text that are directed to actual factual statements and portions of text that include hypothetical descriptions. For example, in the case of medical texts and natural language processing performed in order to facilitate treatment of a patient, it is crucial to be able to distinguish actual events that are important for more accurate treatment suggestions from hypothetical portions of text that may represent possibilities which may lead to erroneous diagnosis and treatment of the patient. Most of the time, medical notes obtain both facts that actually happened, and plans, or hypotheticals, that were discussed with the patient. For example, a patient's electronic medical record (EMR) may have laboratory reports indicating that a particular laboratory test was performed and specific results were obtained from the laboratory test. This would be an example of an actual factual event occurring with regard to the patient. In addition, the doctor may have their own notes in the patient electronic medical record indicating potential procedures or events that the doctor discussed with the patient, e.g., "We recommended that the patient have a mammogram performed." Such potential procedures or events did not actually happen but represent potential plans for the patient that were discussed with the patient and thus, are in fact hypothetical in nature since it is not known at the point that the note was added to the patient's EMR whether the patient will have the procedure or event occur.

For a cognitive system, such as the IBM Watson™ cognitive system available from International Business Machines Corporation of Armonk, N.Y., actual facts are the most important part of such medical texts since the treatment recommendations are based on actual events and facts rather than planned actions or non-implemented actions, possible events, and the like, which may be documented in the medical text yet do not represent actual events or facts, i.e. they instead represent hypotheticals. In order to increase the accuracy of such cognitive systems, it would be beneficial to be able to distinguish portions of textual content representing hypotheticals from portions of textual content representing actual facts and events, and then base the treatment recommendations generated by the cognitive system on the portions representing actual facts and events.

The illustrative embodiments provide mechanisms for ingesting electronic texts, documents, or other portions of textual content and analyzing the textual content to distinguish portions of the text directed to hypotheticals from portions of text directed to actual facts or events that actually occurred. For purposes of the following description, illustrative embodiments will be provided that are directed to the implementation of the present invention in the context of medical texts and a cognitive medical treatment recommendation system. It should be appreciated that the present invention may be implemented with regard to any types of text of various domains without departing from the spirit and scope of the present invention. Thus, for example, the mechanisms described hereafter may be implemented with regard to judicial text or any other type of text which may include hypothetical portions and factual portions and where the distinguishing between hypothetical portions and factual portions of text is subsequently used to perform an analytical, cognitive, or other processing of the text to generate a result.

In the context of a medical treatment recommendation system embodiment in which the mechanisms of the illustrative embodiments distinguish factual portions of text from hypothetical portions of text, the mechanisms of the illustrative embodiments may ingest various types of medical texts and apply the mechanisms of the illustrative embodiments to these medical texts. These medical texts may include, for example, patient electronic medical records (EMRs) in which medical service providers, e.g., doctors, nurses, hospitals, medical laboratories, pharmacies, medical insurance companies, and the like, may contribute content for inclusion in the EMR. As such, the medical text from each of these sources may contain both facts (actual occurrences, events, or results) and hypotheticals, i.e. plans or other possibilities that did not in actuality occur.

In some instances, a single statement or medical text may contain both facts and hypotheticals, such as in the example statement "Given her node positivity and lack of comorbidities, we recommend neoadjuvant therapy." In such a case, while making a treatment recommendation for a patient, it is desirable to know the fact that the patient has node positivity and a lack of comorbidities. However, it is also crucial for the treatment recommendation system to know that the patient has not actually undergone neoadjuvant therapy rather than interpret this portion of the statement as factual as well, i.e. rather than the system thinking that the patient has actually undergone neoadjuvant therapy, the system must be able to determine that this portion of the statement is referring to a recommendation of a future plan (hypothetical) rather than a fact of an event that occurred, and thus can ignore this portion of the statement or simply treat this portion differently from the rest of the text.

In order to distinguish portions of medical text that are describing actual facts from portions of text that are directed to hypotheticals, the illustrative embodiments provide mechanisms implementing a generalizable approach that does not make assumptions of sentence structure. The illustrative embodiments utilize two sets of dictionary data structures that include one set of dictionary data structures directed to identifying terms and phrases corresponding to hypothetical portions of content which a medical treatment recommendation cognitive system may ignore when performing medical treatment recommendation analysis, and a second set of dictionary data structures directed to distinguishing terms and phrases associated with factual portions of content which should be used as a basis for performing such medical treatment recommendation analysis. In addition, parse trees are utilized that include an enhanced representation of textual content against which the dictionaries are applied. A span of an annotation (e.g., hypothetical or factual annotation) is determined by looking at the sub-tree rooted by a matching dictionary entry. Thus, if a node of the parse tree matches a hypothetical term or phrase in the hypothetical dictionary data structures, then the sub-tree rooted by the matching hypothetical term or phrase may be annotated to be hypothetical and may essentially be ignored by the medical treatment recommendation cognitive system when generating a medical treatment recommendation. The approach implemented by the mechanisms of the illustrative embodiments is easy to tune for previously unseen cases, such as by means of different or updated dictionaries of hypothetical terms/phrases.

The illustrative embodiments may operate in a backend portion of the medical treatment recommendation system where natural language processing of medical texts is performed. In the backend system, the medical texts are analyzed using several natural language processing models including one or more models implementing one or more illustrative embodiments of the present invention. The result of such analysis is a set of annotated medical texts that may be utilized by the medical treatment recommendation cognitive system both with regard to machine learning and with regard to actual application to specific patient EMRs for providing specific patient medical treatment recommendations.

In still further illustrative embodiments, personalization of the identification of hypotheticals in medical texts is implemented. That is, in these further illustrative embodiments, it is recognized that different authors, institutions, or other sources of medical texts may utilize language in different ways and thus, a hypothetical term/phrase indicating a hypothetical span of text for one author may not be a hypothetical term/phrase for another author. The illustrative embodiments provide additional mechanisms for evaluating candidate hypothetical terms/phrases to determine a confidence that for the particular author the candidate hypothetical term/phrase is or is not in fact associated with a hypothetical span of text. These additional mechanisms evaluate the writing style of the author, any institutional mandated writing styles, and the like, and generate a confidence score for the candidate hypothetical term/phrase. Comparing the confidence score for the candidate hypothetical term/phrase to a predetermined threshold allows the system to determine whether the candidate hypothetical term/phrase is in fact an actual hypothetical term/phrase for this author. This information may be used along with the other mechanisms of the other illustrative embodiments to distinguish hypothetical spans of text in a medical text from factual spans of text. Moreover, in some illustrative embodiments, these additional mechanisms may be used to generate individual personal hypothetical dictionary data structures for individual authors which can then be used as a basis for performing the differentiation of hypothetical spans of text from factual spans of text in medical text input.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for analyzing medical texts and distinguishing hypothetical portions of text from factual portions of text, as well as annotating such portions of text so that they may be included or excluded from further consideration by the medical treatment recommendation cognitive system when performing its machine learning and/or medical treatment recommendation operations. The mechanisms of the illustrative embodiments improve the accuracy of the medical treatment recommendation cognitive system by informing the system of what portions the system can accurately rely on as indicative of actual facts as opposed to potential facts, i.e. hypothetical facts that cannot be relied upon. In this way the medical treatment recommendation cognitive system is able to base its final medical treatment recommendations on the factual events and not be erroneously affected by the hypothetical portions of medical text.

The mechanisms of the illustrative embodiments utilize a hybrid approach that involves both the use of specially constructed sets of dictionary data structures as well as parse tree data structures. The specially constructed sets of dictionary data structures comprise a set of hypothetical dictionary data structures that specify terms or phrases that are indicative of hypothetical portions of content, with these terms or phrases in the set of hypothetical dictionary data structures being referred to herein as "ignore triggers." The specially constructed sets of dictionary data structures further comprise a set of factual dictionary data structures that specify terms or phrases that are indicative of factual portions of content, with these terms or phrases in the set of factual dictionary data structures being referred to herein as "confirm triggers." The ignore triggers and confirm triggers are combined with a systemic view of a portion of textual content, e.g., a document, paragraph, sentence, phrase, etc., obtained from a parse tree, which enables a more generalizable approach.

The combination of the ignore/confirm triggers with the parse trees allows for portions of the parse trees to be identified as corresponding to hypothetical portions of content, also referred to herein as hypothetical spans, and other portions of the parse trees being associated with factual portions of content, also referred to herein as factual spans. These various spans may be annotated as hypothetical/factual in metadata associated with these portions of content. The annotated spans or portions of the content may then be processed by the medical treatment recommendation cognitive system so as to ignore the portions of content corresponding to hypothetical spans, e.g., zero weightings may be applied to these portions of content or logic may be provided for providing other evaluation of the information in hypothetical spans as plans of medical professionals. In some illustrative embodiments, the annotations contained within hypothetical spans could be removed so as to generate a pruned parse tree which is provided to the medical treatment recommendation cognitive system for use in performing its treatment recommendation cognitive operations. In still other illustrative embodiments, rather than giving the hypothetical spans zero weight or pruning these spans from the parse tree, a relatively lower weight may be given to the annotations inside these spans than to annotations within factual spans so as to still allow some influence from the hypothetical spans to be provided but mitigating their influence by weighting them relatively lower, Thus, rather than these portions of content being considered by the medical treatment recommendation cognitive system as representing evidence upon which the medical treatment recommendation cognitive system may base its treatment recommendations, and thereby potentially generate erroneous medical treatment recommendations, the medical treatment recommendation cognitive system may instead recognize these portions as not being indicative of facts associated with the patient but rather potential facts that are not indicative of the patient's current status and cannot be relied upon, or can be relied upon with less assurance. To the contrary, in some illustrative embodiments, the medical treatment recommendation cognitive system performs its operations only on the portions of content corresponding to the factual spans. In other illustrative embodiments, while the hypothetical spans may still be considered, their relative lack of trustworthiness may be quantified by providing a relatively lower weight or significance to the information obtained from these hypothetical spans than other factual spans.

In some illustrative embodiments, the identification of hypothetical spans of text is personalized to the particular author, institution, or other source of the medical text being analyzed. For example, different terms/phrases used as triggers for identifying hypothetical spans of text may be identified for each author so as to modify a default or general set of terms/phrases used as triggers for identifying a hypothetical span of text. These personalized terms/phrases used as hypothetical triggers, or ignore triggers, may be determined through analysis of each author's personal writing style, any institution required styles associated with the author, evaluations of frequency of use of terms/phrases used to represent hypothetical spans of text, and the like. For example, for each candidate hypothetical term/phrase, these various style features may be evaluated to generate a confidence score indicating the confidence that the system has in the candidate hypothetical term/phrase being an actual indicator, or trigger, of a hypothetical span of text. If this confidence score reaches or exceeds a predetermined threshold value, then the candidate hypothetical term/phrase may be considered an actual hypothetical term/phrase for this particular author.

Such an evaluation may be used to generate a personalized hypothetical dictionary data structure for the author which may include a combination of general hypothetical terms/phrases as triggers as well as personalized hypothetical terms/phrases as triggers. Moreover, some general hypothetical terms/phrases may be removed from this personalized hypothetical dictionary data structure if it is determined that there is little confidence that that term/phrase is in fact used by this particular author to indicate a hypothetical span of text. Thus, for example, it may be generally considered that the term "results" is a hypothetical term/phrase, however for this particular author it may be determined based on an evaluation of the author's style features that the author does not use the term "results" to indicate hypothetical spans of text and instead uses it to refer to actual factual statements or portions of statements. Thus, the term "results" would be removed from the author's personalized hypothetical dictionary data structure.

In one illustrative embodiment, an initial analysis is performed on a portion of medical text based on a generalized hypothetical dictionary data structure to determine if the portion of medical text includes any potential hypothetical spans of text. If so, then the potential, or candidate, hypothetical spans of text are subjected to further analysis based on the personalized writing style of the author, institution, and/or the like. The further analysis compares terms/phrases in the potential or candidate hypothetical span with hypothetical triggers or tuple patterns provided in the personalized hypothetical dictionary data structure to generate a confidence score based on a degree of matching, potentially weighted based on the particular triggers or portions of tuple patterns that are matched, with the confidence score being indicative of whether the potential, or candidate, hypothetical span is in fact associated with a hypothetical portion of text. The higher the confidence score, the more likely the potential hypothetical span is in fact a hypothetical span of text. If the confidence score reaches or exceeds a predetermined threshold level of confidence, then it can be determined that the potential, or candidate, hypothetical span is an actual hypothetical span of text and the additional operations described hereafter for annotating and/or pruning the hypothetical spans may be performed. Thus, in addition to generalizable criteria for hypothetical span identification, the illustrative embodiments provide further mechanism for personalizing the identification to the particular author, institution, and/or other organization.

Figure 2:
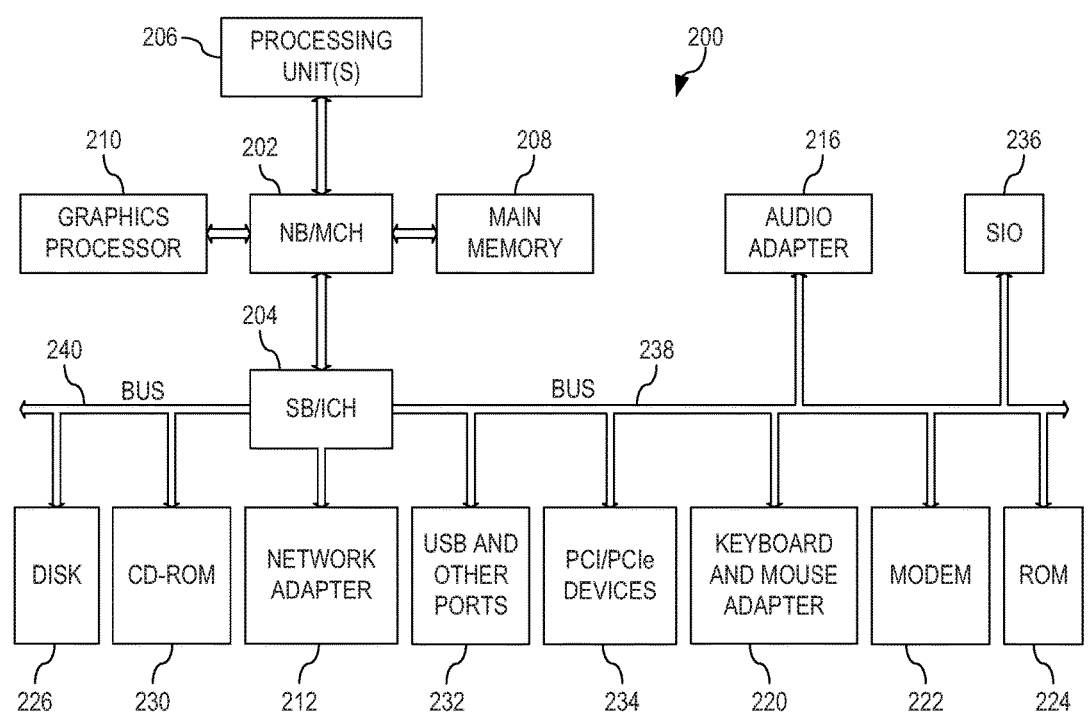
FIG. 2 is a block diagram of an example data processing system in which aspects of the illustrative embodiments are implemented.
Figure 3:
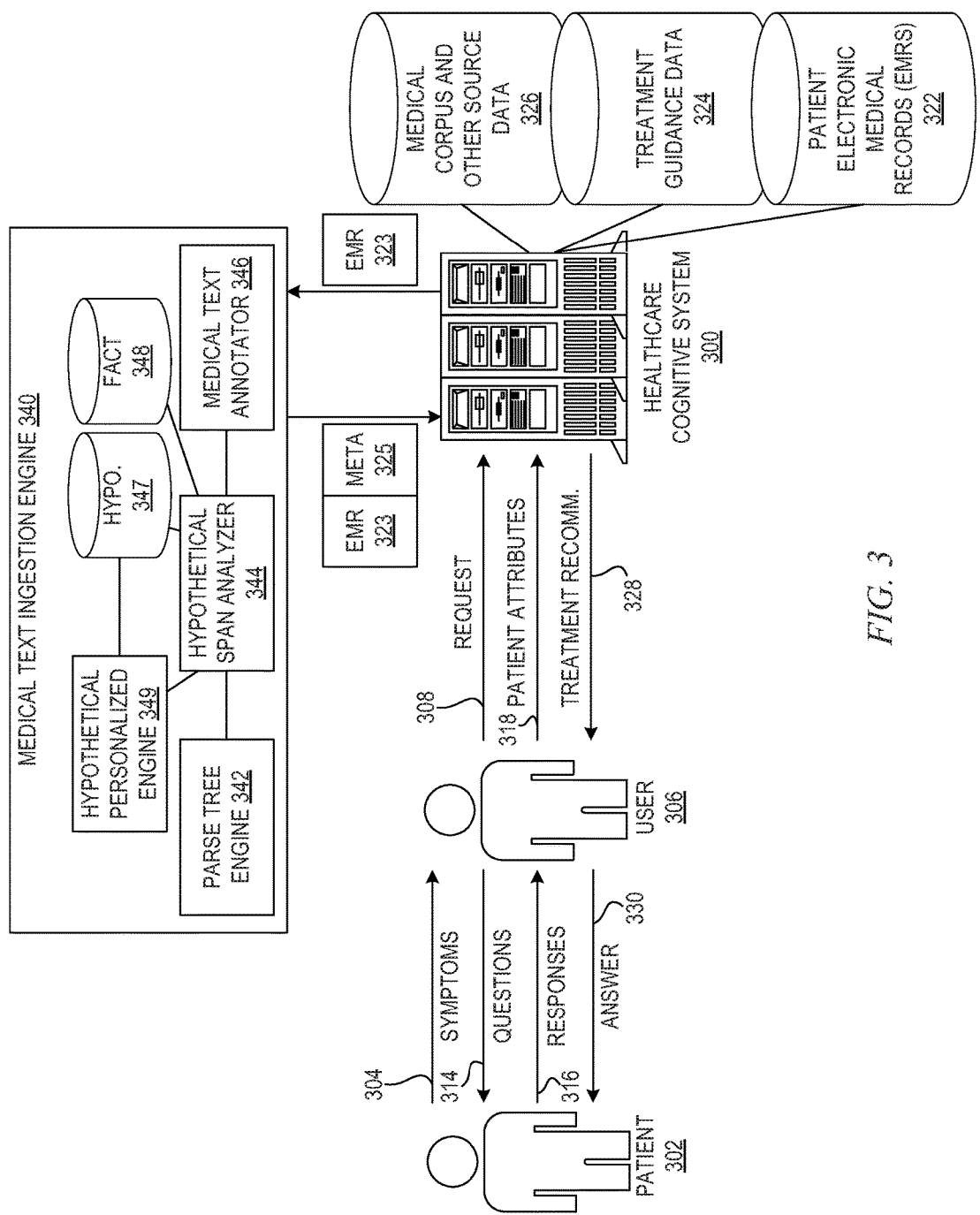
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations and thus, the healthcare cognitive system may also be referred to as a medical treatment recommendation cognitive system herein.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to annotating ingested medical texts and operating on these ingested medical texts to perform healthcare based operations that distinguish between hypothetical portions of medical text and factual portions of medical texts. In particular, in some illustrative embodiments, the medical texts may comprise patient electronic medical records (EMRs) and the healthcare based operations may comprise providing a medical treatment recommendation based on the EMRs of a patient. In this way, the healthcare cognitive system provides a decision support system directed to medical treatment recommendations.

In view of the above, it is important to first have an understanding of how cognitive systems, and question and answer creation in a cognitive system implementing a QA pipeline, is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding

Ingest and process vast amounts of structured and unstructured data

Generate and evaluate hypothesis

Weigh and evaluate responses that are based only on relevant evidence

Provide situation-specific advice, insights, and guidance

Improve knowledge and learn with each iteration and interaction through machine learning processes Enable decision making at the point of impact (contextual guidance)

Scale in proportion to the task

Extend and magnify human expertise and cognition

Identify resonating, human-like attributes and traits from natural language

Deduce various language specific or agnostic attributes from natural language

High degree of relevant recollection from data points (images, text, voice) (memorization and recall)

Predict and sense with situational awareness that mimic human cognition based on experiences Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, subsystems, and/or devices other than those that are depicted herein.

The cognitive system 100 is configured to implement a QA pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 3.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process is repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

In one illustrative embodiment, the cognitive system 100 is a medical treatment recommendation system that analyzes a patient's EMR in relation to medical guidelines and other medical documentation in a corpus or corpora of information to generate a medical treatment recommendation as to how to treat a medical malady or condition of the patient. In other illustrative embodiments, the domain may be a judicial domain with the cognitive system 100 providing cognitive analysis of hypotheticals and factual statements regarding legal cases and legal text. For example, the cognitive system 100 may provide recommendations based on distinguishing hypotheticals in victim, witness, or accused records, statements, and the like. For example, the statements "The victim's phone was in the car. We believe the victim placed her phone in the car" may be analyzed using the mechanisms of the illustrative embodiment to distinguish the fact that the victim's phone was in the car from the hypothetical that the victim himself/herself actually placed the phone in the car. Recommendations or other cognitive or algorithm operations may then be performed based on the distinguishing of factual portions from hypothetical portions.

As shown in FIG. 1, and again with reference to a medical treatment recommendation cognitive system implementation, the cognitive system 100 is further augmented, in accordance with the mechanisms of the illustrative embodiments, to include logic implemented in specialized hardware, software executed on hardware, or any combination of specialized hardware and software executed on hardware, for implementing a medical text ingestion engine 120 that itself implements a parse tree engine 122, hypothetical span analyzer 124, and medical text annotator 126. Moreover, the hypothetical span analyzer 124 has associated hypothetical dictionary data structures 127 and factual dictionary data structures 128 that the hypothetical span analyzer 124 utilizes to identify hypothetical and factual spans within a parse tree, as described hereafter.

In addition, the medical text ingestion engine 120 may include a hypothetical personalization engine 129 which operates to evaluate author, institution, and other organizations or sources of medical texts, natural language content, and the like, with regard to the styles, both in terms of content and structure, and term/phrase usage to generate a personalized profile of hypothetical evaluation criteria for the particular author, institution, organization, or other type of source (hereafter collectively referred to simply as a "source"). In some illustrative embodiments, this may involve generating a personalized hypothetical dictionary data structure for the source which may be included as part of the hypothetical dictionary data structures 127. The personalized profile and/or personalized hypothetical dictionary data structure may be applied to portions of text that are candidates for being hypothetical spans of text to determined, based on the writing style of the source, whether these are indeed actual hypothetical spans of text. In this way, individual writing styles of sources may be considered when determining whether a particular term or phrase in a portion of text is in fact referring to a hypothetical statement or portion of a statement.

The medical text ingestion engine 120 may operate on any medical textual content present in the corpus 130 and operates on this medical text go annotate the medical text as part of an ingestion operation. The ingestion operation generates an in-memory representation of the medical text for use by the cognitive system 100 when performing its cognitive operations, such as a healthcare based cognitive operation utilizing pipeline 108. These medical texts may include medical guideline documents, medical position papers, health insurance guidelines, or any other medical information in which factual and/or hypothetical statements may be present. In some illustrative embodiments, the medical texts in corpus 130 may comprise a patient registry having patient electronic medical records (EMRS) for one or more patients stored therein. These patient EMRs may comprise information obtained from a variety of different sources of medical information for the patient(s) including doctor generated EMRs, institution generated EMRs (such as from a medical practice, hospital, urgent care facility, etc.), pharmacy generated records, medical laboratory records, and the like. This information may be compiled together into an EMR for the patient or set of EMRs for the patient. Alternatively, this information may be separately stored in separate data structures associated with an identifier of the patient.

The medical texts, as noted above, may comprise both factual and hypothetical portions of content. The medical text ingestion engine 120 operates to retrieve such medical texts from the corpus 130, such as in response to a received request or as part of a general ingestion operation occurring prior to the receipt of a specific request. For example, the cognitive system 100 may receive a request to generate a medical treatment recommendation for a specified patient. In response, the cognitive system 100 may request that the medical text ingestion engine 120 ingest the specified patient's EMRs from the corpus 130. Alternatively, a plurality of EMRs for a plurality of patients in the patient registry of the corpus 130 may be ingested as part of an initialization or periodic process of the medical text ingestion engine 120. In either case, the medical text ingestion engine 120 operates on the medical text of the patient EMRs, or other medical texts as the case may be, to distinguish between hypothetical portions of content (hypothetical statements or phrases) in the medical text and factual portions of content. The medical text is annotated accordingly by adding annotations to the metadata associated with the medical text. The annotated medical text may be provided to the cognitive system 100 as an in-memory representation of the medical text upon which the cognitive system 100 may perform its cognitive operations.

In order to generate the annotated medical text, the medical text is received or retrieved by the medical text ingestion engine 120 from the corpus 130. The medical text is then parsed by the parse tree engine 122 using logical parsing techniques to generate a parse tree. An example of a mechanism for generating a parse tree from natural language text, such as the medical text obtained from corpus 130, may be the mechanism described in co-pending and commonly assigned U.S. patent application Ser. No. 14/506, 855, filed Oct. 6, 2014, and entitled "Natural Language Processing Utilizing Logical Tree Structures." While this is one example of a mechanism for generating a parse tree for natural language statements, the illustrative embodiments herein are not limited to implementations utilizing the mechanisms of this commonly assigned and co-pending patent application and other mechanisms for generating parse trees of natural language content may be used without departing from the spirit and scope of the present invention.

Regardless of the particular parsing techniques utilized by the parse tree engine 122, the resulting parse tree data structures, generated by the parse tree engine 122 based on the analysis of the medical text, provide structural representations of portions of textual content in the medical texts, e.g., sentences in the medical text. The parse tree provides a hierarchical visualization of the portion of textual content, e.g., sentence, enabling the inferring of relationships between tokens, i.e. words or phrases corresponding to nodes of the parse tree.

The hypothetical span analyzer 124 implements a hybrid technique for searching the parse tree data structure for tokens matching ignore triggers or confirm triggers specified in the hypothetical dictionary data structures 127 (ignore triggers) and factual dictionary data structures 128 (confirm triggers). The hypothetical dictionary data structures 127 specify those terms and phrases that are indicative of a hypothetical statement or hypothetical portion of a statement. The factual dictionary data structures 128 specify those terms and phrases that are indicative of a factual statement or portion of a statement. Again, a hypothetical is an indication of a fact that has not actually occurred, such as an action, event, designation of state or condition, or other potential occurrence that has not in fact actually occurred. A fact, on the other hand, is something that has actually happened, i.e. an event, action, designation of state or condition, or other type of occurrence that has actually occurred. In the context of medical texts, hypotheticals often times are associated with future plans or potential conditions/outcomes associated with a patient's treatment that may or may not later occur. On the other hand, facts are associated with the current or past condition of the patient, current or past procedures performed on the patient, and other patient condition or state information and event information that actually occurred.

For example, the hypothetical dictionary data structure 127 may include an entry that identifies the term "discussed" as an ignore trigger. That is, it has been determined that the term "discussed" when used in medical texts, such as a patient's EMR, indicates a potential future event since it often refers to the doctor discussing with the patient possible treatments or possible conditions or states of the patient that did not in fact happen yet, e.g., "I discussed performing a nipple-sparing mastectomy with the patient". Thus, instances of the term "discussed" are triggers for ignoring portions of medical text that are associated with the term "discussed." It should be appreciated that a large set of ignore trigger terms and phrases may be identified as indicative of hypotheticals, such as "recommended", "advised", and "planned," and the like, and may be included in the hypothetical dictionary data structure 127.

Similarly, the factual dictionary data structure 128 may include an entry that identifies the term "revealed" as a confirm trigger. That is, it has been determined that the term "revealed" when used in medical texts, such as a patient's EMR, indicates an actual event, state, or condition of the patient that has occurred, e.g., "Results of the biopsy revealed that the tumor was malignant." Thus, instances of the term "revealed" are triggers for confirming portions of medical text as being associated with factual statements or factual portions of statements. It should be appreciated that a large set of confirm trigger terms and phrases may be identified as indicative of factual statements or portions of statements, such as "resulted", "results," "the patient has", and the like, and may be included in the factual dictionary data structure 128.

The hypothetical span analyzer 124 uses the hypothetical dictionary data structure 127 and factual dictionary data structure 128 to search the parse tree data structure generated by the parse tree engine 122 to identify instances within the parse tree data structure of tokens associated with nodes that match the ignore triggers or confirm triggers. Both sets of triggers are searched for in the parse tree data structure and corresponding spans of text are then identified based on the parse tree and the matching nodes. The spans are identified as the sub-trees of the nodes matching the particular trigger. Thus, a hypothetical span is the sub-tree portion of the parse tree data structure corresponding to a node matching an ignore trigger. A factual span is the sub-tree portion of the parse tree data structure corresponding to a node matching a confirm trigger. It can be the case that a factual span may be found within a hypothetical span in which case the factual span are removed from the hypothetical span and are considered to be associated with a confirm trigger and thus, directed to a factual portion of text. The operations performed by the hypothetical span analyzer 124 will be described in greater detail hereafter.

The hypothetical span analyzer 124 identifies the hypothetical and factual spans within the parse tree data structure generated by the parse tree engine 122 and provides this information to the medical text annotator 126. The medical text annotator 126 processes the hypothetical spans and creates annotations (metadata) based on the sub-tree of the parsed medical text that denote which portions of the medical text are associated with hypothetical statements, or hypothetical portions of statements, and which portions of the medical text are associated with factual statements, or factual portions of statements. The medical text annotator 126 performs noun-verb disambiguation for trigger terms based on the tuples found in the hypothetical spans and the comparison to their usage in a parse tree pattern. In other words, the output of hypothetical span analyzer 124 is used by medical text annotator 126 to find a way to treat the annotations within hypothetical spans, e.g., ignoring all annotations associated with hypothetical spans, converting annotations associated with hypothetical spans to other annotations, or the like. These annotations may be provided in addition to other annotations generated by other annotators operating on the medical text and may be stored in metadata associated with the medical text. This metadata may be stored as a separate but associated data structure or may be stored as a portion of the data structure housing the medical text content, e.g. as part of the patient EMR data structures. It should be appreciated that once this operation is performed on a portion of a patient's EMR data structure, the operation need not be performed again since the metadata specifically identifies which portions of the EMR data structure are hypothetical and which are not. However, the mechanisms of the illustrative embodiments may operate on the patient EMR again in cases where new content has been added to the patient EMR, modifications to the dictionaries 127-128 are performed, or the like.

In some illustrative embodiments, the hypothetical span analyzer 124 may employ the logic of the hypothetical personalized engine 129 to evaluate potential hypothetical spans with regard to the personal writing style of the source of the medical text. That is, the hypothetical personalization engine 129 may learn, through a machine learning process, the personal style of a particular source by evaluating the features of textual content from that source and generating a machine representation of that source's writing style, both with regard to content and structure, and term/phrase usage. The writing style information learned by the hypothetical personalization engine 129 may then be applied to portions of the parse tree data structure identified as being associated with ignore triggers, i.e. hypothetical or ignore sub-trees of the parse tree corresponding to potential hypothetical spans of text. The application of the writing style information to such candidate hypothetical or ignore sub-trees results in a confidence score indicating a confidence in the determination that the sub-tree is in fact a hypothetical or ignore sub-tree taking into consideration the personal writing style of the source. This confidence score may then be compared to a threshold to determine if the threshold is met or exceed at which point it may be determined with confidence that the sub-tree is in fact a hypothetical or ignore sub-tree for this particular source.

With regard to writing style, various features of writing style may be evaluated by the hypothetical personalization engine 129 with regard to a single or multiple portions of textual content provided by the source. For example, the writing style of a source may be evaluated with regard to a "within sentence style" or personal observed pattern in which patterns of usage of passive voice, subject, verb, object correspondence, and other sentence structure patterns used by the source. The writing style patterns may be determined by statistical analysis of existing documents, e.g., medical texts, notes, etc., both with regard to single sentences and multiple sentence levels, e.g., statistical analysis to determine the most frequent words the source uses, statistical analysis to determine whether the source always follows a fact with a discussion phrase or sentence, analysis of the tone of a sentence or multiple sentences, etc. In evaluating a potential hypothetical span of text, if the hypothetical span of text corresponds with the general writing style of the source in this regard, then the confidence score that the hypothetical span of text is an actual hypothetical span of text is increased. Otherwise, if the styles do not correspond, then the confidence score may be decreased.

In addition, the structure of the medical text itself may also be analyzed to determine sections of the medical text and identify sections of the medical text where hypothetical statements or portions of statements are likely to be present. For example, for a particular source, hypothetical plans may typically be followed by observations and thus, if a sentence includes a first portion and a second portion, where the second portion is an observation and the first portion is a potential hypothetical span of text, then a confidence that the potential hypothetical span of text may be increased for the first portion. Moreover, sections of the medical text may be identified that correspond to particular fields, titles, or the like, and those fields, titles, and the like may have associated expectations as to whether their content is hypothetical or non-hypothetical, e.g., a field whose content is for future recommendations, then this will be more highly scored as confident that the content of this field is hypothetical. If the field is for describing particular results of an examination of the patient, then the score associated with the content of this field will be scored less highly with regard to confidence that the content of the field is hypothetical.

Furthermore, institutional or organizational rules defining an institutional or organizational style may be evaluated to determine increases/decreases in the confidence that a particular hypothetical span of text is in fact hypothetical. For example, an institution may require that medical texts be composed in a particular manner and this style may be indicative of whether a corresponding portion of text is hypothetical in nature or not. Thus, for example, the institution may indicate that recommended treatments be specified with a particular wording or in a particular portion of a medical text and this style information may be maintained and used to score the confidence in a particular portion of text as to whether it is hypothetical or not. If the portion of text corresponds to a style of the institution or organization, e.g., a rule, that is indicative of a hypothetical portion of content, then the confidence score is increased. If the portion of text corresponds to a style of the institution or organization, e.g., a rule, that is indicative of a factual portion of content, then the confidence score may be decreased.

In some illustrative embodiments, the hypothetical personalization engine 129 may be employed to generate a separate instance of the hypothetical dictionary data structure 127 for each source that is personalized to the particular term/phrase usage of the source. That is, through analysis of textual content authored by the source, a frequency of utilization of terms/phrases with regard to hypothetical spans of text may be measured and compiled. Based on this frequency, terms/phrases may be added/removed from the instance of the hypothetical dictionary data structure 127 for this particular source. Thus, if a particular term/phrase is used by this source frequently, e.g., above a predetermined threshold number of times, in textual content to reference hypothetical statements or portions of statements, then that term/phrase may be added to or maintained in the hypothetical dictionary data structure instances for that source. If it is determined that a particular term/phrase is used more often by this source to refer to factual statements or portions of statements, and that term/phrase appears in the personal instance of the hypothetical dictionary data structure 127 for the source, then that term/phrase may be removed from the personal instance of the hypothetical dictionary data structure 127.

Thus, separate personal instances of the hypothetical dictionary data structure 127 may be generated for each source which are customized to the particular term/phrase usage of that particular source. These personal instances of the hypothetical dictionary data structure 127 may be utilized by the hypothetical personalization engine 129 to further evaluate hypothetical or ignore sub-trees when generating confidence scores where terms/phrases in the personal instance of the hypothetical dictionary data structure 127 matching a node in the identified potential hypothetical or ignore sub-tree are given a higher confidence rating that they are in fact corresponding to a hypothetical or ignore trigger.

For example, with regard to a patient's EMR, the patient EMR may comprise portions of text from various sources, e.g., various doctors, nurses, medical technicians, hospitals, medical laboratories, etc. Each of these sources may have their own writing styles, word choices, ordering or structure of statements, and may have institutional or organizational requirements or rules that dictate the way in which certain types of medical text or content are to be included in a patient's EMR. As a first example, consider the fact that word choices and the frequency by which a source, such as a doctor, uses certain words differs from source to source. Some doctors, for example, may prefer some terms or words over others. Consider the terms "show", "reveal", and "indicate" which all have slightly different meanings and dependent on who uses these words, the semantics may slightly change as well. For a doctor that uses the term "show" for explaining observations, for example, the use of the term "reveal" may be indicative of surprise, confusion, or uncertainty. Thus, the instances of the term "show" for this particular doctor may be indicative of factual spans of text, whereas the term "reveal" may be associated with hypothetical spans of text. This term/phrase preference or pattern of usage of the doctor may be identified through statistical analysis of a plurality of medical texts, notes, documents, or the like, submitted by the doctor, or source. For example, the doctor's contributions to a plurality of patients' EMRs may be analyzed to identify such styles. By identifying such styles for each source, e.g., each doctor or medical personnel, that has added a portion of medical text or content to the patient's EMR, personalized evaluations of confidence in the identification of hypothetical spans of text may be performed with regard to each source and their corresponding additions to the patients' EMR.

As another example, consider that some sources, e.g., doctors, have particular patterns for presenting information which may be identified through statistical analysis of a plurality of portions of medical text or content provided by those sources. For example, different doctors may present facts and observations in a different order. For example, one doctor may present facts before observations, e.g., "This patient has raised skin, they may have a rash," while another doctor may present observations before facts, e.g., "I think this patient has a rash. I checked and they have raised skin." Through statistical analysis of the structure of sentences submitted by a particular doctor, the particular order style of the doctor may be determined, e.g., the doctor presents observations before facts or the doctor presents facts before observations. This information may be leveraged to evaluate the portions of a sentence where a potential hypothetical span of text is presented and either increase or decrease the confidence score associated with that potential hypothetical span of text, e.g., if the potential hypothetical span of text exists in a portion of the sentence corresponding to this doctor's pattern of presenting facts, then the confidence score is decreased, however if the hypothetical span of text exists in a portion of the sentence corresponding to this doctor's pattern or presenting observations, then the confidence score is increased.

As another example, consider an institution's rules or style to present factual spans of text associated with findings of the institution using active rather than passive voice and to present findings of other institutions in passive voice. If the institution's rule is to not accept the facts presented by other institutions as granted, the institution may ignore those portions of medical text that are directed to facts presented by other institutions. Thus, portions of text that utilize passive voice and reference another institution may have their confidence scores associated with a potential hypothetical span of text increased whereas portions of text that utilize active voice and do not reference other institutions may have their confidence scores decreased. For example, consider the statement "The patient consulted INSTITUTION. He was told that he has SCLC." The token "was told" is in passive voice and may be designated in the hypothetical dictionary data structure as an ignore trigger which starts a hypothetical statement. However, the token "he has" is a confirm trigger which ends the hypothetical statement before the confirm trigger starts. If an institution does not want to accept "SCLC" as a fact for the analysis of the patient's EMR, and instead considers it as a hypothetical until confirmed by the current institution's tests, the confidence score that this portion of text is hypothetical may be increased.

It should be noted that in the above illustrative embodiments, the designation of source is provided in the medical text as part of the metadata or as inline notes or comments of the medical text. For example, authorship information may be present in the metadata, institution or organizations with which the medical text is associated may also be included in the metadata, and the like. Sometimes the name of the doctor or medical personnel adding entries to a patients' EMR are included in the content of the entry itself and may be used to identify the source of the medical text, e.g., the note added to the patient's EMR.

Thus a combination of personal writing style features, institutional or organizational writing style features, structure or organization of the text itself, and frequency of terms/phrases used by the source with regard to hypothetical/factual portions of sentences may be used to evaluate the confidence that a portion of text is in fact associated with a hypothetical statement or portion of a statement. This information may be used to make a determination as to whether a candidate hypothetical span of text is in fact an actual hypothetical span of text and can be annotated or pruned as such. As a result, a more accurate annotated medical text data structure and/or pruned parse tree is generated that takes into consideration the personal writing style of the source.

The resulting annotated medical text data structures may be provided to the cognitive system 100 for use in performing a cognitive operation on the medical text. In some illustrative embodiments, these cognitive operations utilize the hypothetical/factual annotations to determine how much to weight each portion of the medical text as part of the cognitive operation. For example, in some illustrative embodiments, portions of the medical texts that are associated with hypothetical annotations in the metadata of the medical texts may be essentially ignored by associated a zero weight factor with these portions of the medical text whereas portions of medical text associated with factual annotations are given a predefined weight which may be modified by other weights for other aspects of the medical text depending on the particular implementation. In some illustrative embodiments, the metadata itself may comprise a pruned parse tree representation of the medical text where the pruned parse tree corresponds to the original parse tree but with sub-trees corresponding to hypothetical spans of text having been removed, or pruned, from the parse tree, thereby causing the cognitive system to ignore those portions of the medical text when performing its cognitive operations.

In one illustrative embodiment, the cognitive operation performed by the cognitive system 100 is a medical treatment recommendation cognitive operation which will ignore the portions of medical text associated with hypothetical annotations and base treatment recommendations only on the portions of medical text associated with factual annotations or portions that are specifically not associated with a hypothetical annotation, e.g., other portions of the medical text that are not associated with either a hypothetical annotation or factual annotation and thus, are indeterminate.

It should be appreciated that while both hypothetical and factual dictionary data structures 127-128 are shown in the depicted embodiment, the illustrative embodiments do not require both types of data structures to be present in order to perform their operations. To the contrary, in some illustrative embodiments, only a hypothetical dictionary data structure 127 may be utilized such that any portions of the parse tree that do not match an ignore trigger, or are part of a sub-tree associated with a node matching an ignore trigger, set forth in the hypothetical dictionary data structure 127, is considered to be associated with a factual portion of content. Thus, in this embodiment, only a search for ignore triggers is performed with anything else in the parse tree being considered factual.

Thus, the illustrative embodiments provide a mechanism for distinguishing between hypothetical portions of textual statements and factual portions of textual statements. Based on this distinction, appropriate annotations are applied to the portions of textual statements which may then be used to modify the cognitive operations performed based on the text. In particular, hypothetical portions of textual statements may be given relatively less weight or consideration than factual portions of textual statements, and in some cases may be completely ignored when performing the cognitive operations on the text.

As noted above, the present invention provides a specific improvement to the way in which a cognitive system operates. Such cognitive systems are implemented on one or more data processing systems or computing devices. FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p° computer system, running the Advanced Interactive Executive) (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases, such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provide a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to include a medical text ingestion engine 340, which may be the medical text ingestion engine 120 in FIG. 1, for example. The medical text ingestion engine 340 operates on one or more of the corpora of data 322-326 to ingest those one or more corpora 322-326 to generate an in-memory representation of the medical texts usable by the healthcare cognitive system 300 to perform its cognitive operations. The ingestion operation comprises analysis of the medical texts to identify various features of the medical texts, such as parts of speech of the various terms and phrases used in the medical text, ontological correlations indicating instances of concepts within the medical text, and other annotation of the medical texts to generate metadata annotations that may be used by the healthcare cognitive system 300 to perform its cognitive operations. Other appropriate processing of the corpora 322-326, as is generally known with regard to cognitive system ingestion mechanisms, may also be implemented as part of the ingestion operation.

In accordance with the illustrative embodiments, the medical text ingestion engine 340 is augmented to include logic for performing analysis to distinguish hypothetical portions of text and factual portions of text in the medical texts of the one or more corpora 322-326. In one illustrative embodiment, the medical text ingestion engine 340 analyzes patient EMRs 322 to distinguish and annotate hypothetical portions of text and factual portions of text. The resulting annotated medical texts may then be utilized by the healthcare cognitive system 300 to perform a cognitive operation, such as a medical treatment recommendation, giving appropriate weight to the hypothetical and factual portions of text, e.g., zero weight to the hypothetical portions and more than zero weight to the factual portions of text.

For example, the medical text ingestion engine 340 may retrieve a patient EMR 323 from the patient EMR corpus 322, which may be a patient registry or the like. The textual content of the patient EMR 323 may then be analyzed by the parse tree engine 342 to generate a parse tree data structure representing the textual content. The parse tree data structure comprises nodes representing tokens in the text, where the token is a term or phrase, and edges connecting the nodes representing relationships between the nodes. Moreover, some nodes may represent logical relationships, e.g., AND, OR, ANDNOT, etc., between portions of the text. Nodes may have associated attributes including parts of speech attributes which may be used to assist the analysis when determining whether a node corresponds to an ignore trigger or confirm trigger, as discussed hereafter.

Figure 4:
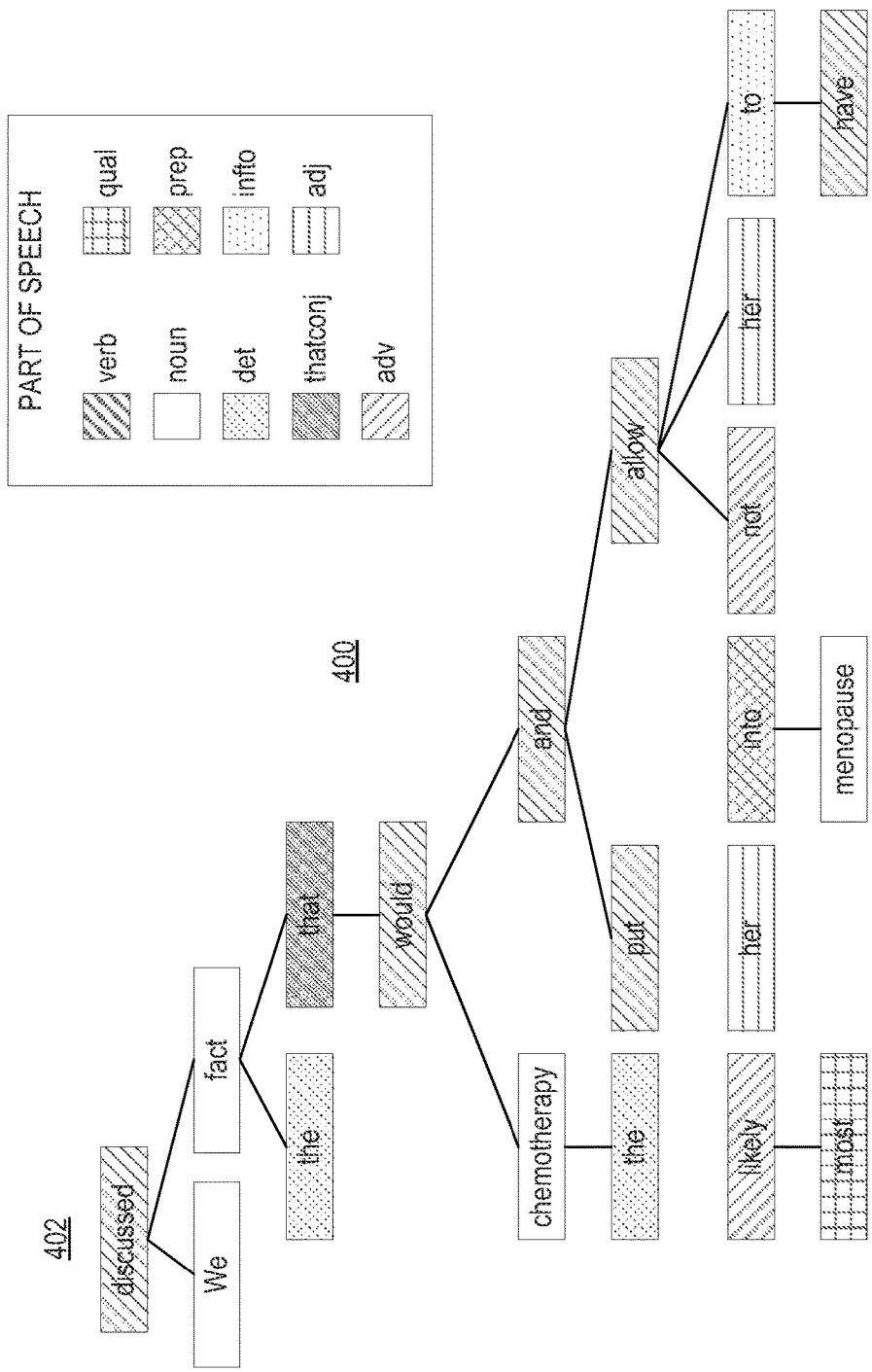
FIG. 4 is an example parse tree data structure representation an example note, composed by a medical professional, which may be part of a patient's electronic medical record (EMR)

For example, FIG. 4 is an example parse tree data structure representation an example note, composed by a medical professional, which may be part of a patient's EMR. In the depicted example, the parse tree is for the statement "We discussed the fact that the chemotherapy would most likely put her into menopause and not allow her to have more children." The generation of the parse tree, as noted above, may be performed using parsing logic such as described in co-pending and commonly assigned U.S. patent application Ser. No. 14/506,855, for example, or other suitable parsing logic.

The parse tree data structure is provided to the hypothetical span analyzer 344 which analyzes each of the nodes of the parse tree data structure to identify nodes matching ignore triggers specified by the hypothetical dictionary data structures 347 and confirm triggers specified by the factual dictionary data structures 348. The hypothetical span analyzer 344, for example, may receive a parse tree data structure for each sentence of the medical text, or depending on the particular implementation, a parse tree for any size portion of text from the medical text retrieved by the medical text ingestion engine 340. For each node in the parse tree data structure, a determination is made as to whether the node's token corresponds to an ignore trigger specified in the hypothetical dictionary data structures 347. If so, the part of speech attribute of the node is compared to a part of speech attribute of the ignore trigger to determine if there is a match in the part of speech with this match being a verb part of speech. If the part of speech attribute of the node is a verb and the node's parent node's part of speech is a verb, then the sub-tree of the node is selected to be an ignore sub-tree with the node's parent node being the root of that ignore sub-tree.

The check for part of speech tag of the parent node is performed in order to determine if the sentence is passive or active, such as a sentence containing "was recommended" indicates a passive sentence. If the trigger is "recommended" and "recommended" is identified as a verb by the parse tree as well as its parent node being "was", the hypothetical subtree starts from "was" instead of "recommended." This is to capture phrases such as "were discussed" where "discussed" is the identified node and "were" is a parent node of the identified node, for example. If the node and the parent node are not both verbs, then the sub-tree of the node is selected with that node being the root of the ignore sub-tree.

The reason that verbs are targeted for this process is that some terms or phrases may be used as multiple parts of speech, e.g., both a noun and a verb. However, in some implementations, hypothetical trigger terms or phrases are more often used as verbs and thus, the identification of a trigger term that is a verb is likely to indicate a hypothetical span of text. It should be appreciated that other implementations may make more complex analysis of the parts of speech and may not be dependent upon whether or not the parts of speech of the node token and the ignore trigger are verbs.

For each node of the ignore sub-tree, a determination is made as to whether the node corresponds to a confirm trigger. If a node of the ignore sub-tree matches a confirm trigger, then the sub-tree of that node is selected and that confirm sub-tree is removed from the ignore sub-tree. The resulting ignore sub-tree with any confirm sub-trees removed, is returned for annotation with an ignore annotation, or hypothetical annotation, while the confirm sub-trees are returned for confirm, or factual, annotations. Trees or sub-trees of the parse tree data structure that do not correspond to an ignore sub-tree may also be annotated with a confirm annotation, or factual annotation, or may otherwise not be annotated with regard to confirm/ignore annotations, depending on the particular implementation.

If it is determined that the part of speech of the token of the node matching an ignore trigger is a noun and not a verb, additional analysis of other natural language resources corresponding to the token of the node may be analyzed to generate a confidence score as to whether or not the token of the node is likely indicative of a hypothetical. For example, definition information from a dictionary data structure indicating the part of speech of the various uses of the token and the tense information for the various uses, n-grams, and the like may be analyzed to generate a score of the likelihood of the token being indicative of a hypothetical span of text and thus, matching the ignore trigger. This analysis is performed since the same token may represent both an ignore trigger and a confirm trigger depending on the way in which the token is utilized in the text. As an example, consider the term "considering" in the following sentences:

1. The patient has been strongly considering a prophylactic mastectomy on the right breast for ultimate risk reduction.
2. The patient has been advised considering the prophylactic mastectomy on the right breast for ultimate risk reduction.

In sentence 1 above, the term "considering" is an ignore trigger as it is describing a hypothetical future possibility of the patient undergoing a prophylactic mastectomy. In sentence 2 above, the term "considering" is a confirm trigger as the term is referring to an actual event that occurred, i.e. the medical professional advising the patient about the prophylactic mastectomy. In sentence 2, noun-verb disambiguation is performed based on the part of speech and tense information associated with the tokens and part of speech and tense information in the dictionary to determine whether the instance of the token "considering" is an ignore trigger or confirm trigger.

The n-grams used to disambiguate these two sentences will be different: <noun><adverb> considering <noun-procedure> and <noun><verb> considering <noun-procedure>. Because the first sentence matches the tuples in a training set, sentence 1 will be identified as hypothetical whereas sentence 2 is not.

Returning to FIG. 4, the sentence corresponding to the parse tree 400 shown in FIG. 4 illustrates a simple example of a sentence with an ignore trigger and corresponding ignore sub-tree that does not comprise an embedded confirm sub-tree. As shown in FIG. 4, the node 402 having token "discussed" is matched to a corresponding ignore trigger in the hypothetical dictionary data structures 347. Taking this node 402 as a root node of an ignore sub-tree comprising the child nodes of the node 402, the hypothetical span analyzer 344 searches the ignore subtree for any confirm trigger matches that are a sibling or child of the "discussed" node 402 but there are none in this example. As a result, the whole tree 400 rooted with the "discussed" node 402 is selected as an ignore sub-tree and flagged for annotation with an ignore or hypothetical annotation by the medical text annotator 346.

The annotated ignore sub-tree 400 may then be processed by the healthcare cognitive system 300 to perform a cognitive operation with appropriate weighting given to the ignore sub-tree 400. In some illustrative embodiments, this weighting involves ignoring the ignore sub-tree 400 when performing the corresponding cognitive operation. In some illustrative embodiments, this cognitive operation is a machine learning operation performed by a machine learning model of the healthcare cognitive system used with regard to medical treatment recommendations. In some illustrative embodiments, this cognitive operation is the operation of providing the medical treatment recommendation to a user request 308. In other illustrative embodiments, other cognitive operations that may be affected by the validity, trust, or confidence attributed to hypothetical spans of text, may operate based on the hypothetical (or ignore) annotations and factual (confirm) annotations generated by the mechanisms of the illustrative embodiments.

It should be noted that, in some illustrative embodiments, prior to acceptance of the ignore sub-tree as an actual ignore sub-tree or hypothetical sub-tree, further evaluation of the ignore/hypothetical sub-tree may be performed based on the personal profile and personal dictionary data structures associated with the source of the portion of text being analyzed. Returning to FIG. 3, the hypothetical personalization engine 349 may comprise personal profiles for each of the sources encountered in the corpora 342-346. These personal profiles have learned writing style features set forth in the profile that indicates the personal writing style of the particular source. Such writing styles may include organization and structure features indicative of the way in which the source presents information as well as various language features frequently used by the source. The analysis of natural language to extract features of writing style is generally known in the art but has not been applied to the evaluation of hypothetical spans of text in the manner presented herein. Thus, any known natural language analysis and/or statistical analysis may be used, as discussed above, to evaluate and determine writing style features of a particular source.

The profile of a source of the candidate or potential ignore sub-tree may be applied against the portion of text corresponding to the ignore sub-tree to determine if the profile supports or refutes the finding that this portion of text corresponds to a hypothetical span of text. Examples of writing style features supporting/refuting hypothetical spans of text have been presented above. Other types of writing style comparisons to determine support/non-support of the finding of a portion of text being directed to a hypothetical will be readily apparent to those of ordinary skill in the art in view of the present description and are intended to be within the spirit and scope of the present invention. Thus, based on the application of the profile to the portion of text, a confidence score is generated as to the confidence that the candidate or potential ignore sub-tree is an actual ignore subtree corresponding to a hypothetical portion of text for this source.

In addition, a personalized hypothetical dictionary data structure, such as may be maintained by the engine 349 or the hypothetical dictionary data structures 347, may be retrieved and compared to the ignore trigger found in the parse tree and associated with the candidate or potential ignore sub-tree. If the ignore trigger matches a personalized ignore trigger in the personalized hypothetical dictionary data structure, then the confidence score may be increased. If the ignore trigger does no match a personalized ignore trigger in the personalized hypothetical dictionary data structure, then the confidence score may be decreased.

The confidence score may be compared by the hypothetical personalization engine 349 to a threshold confidence score value to determine if this threshold is met or exceeded. If so, then the candidate or potential ignore sub-tree is considered to be an actual ignore sub-tree for this particular source. If the confidence score is less than this threshold, then the candidate or potential ignore sub-tree may be considered to not be an actual ignore sub-tree and further processing of the candidate or potential ignore sub-tree as an ignore sub-tree may be discontinued. This does not necessarily mean that the candidate or potential ignore sub-tree is annotated as being factual, but instead the portion of text may not be annotated hypothetical or factual. While this may mean that the healthcare cognitive system will operate on the portion of text as if it were factual, in embodiments where different weights are applied by the healthcare cognitive system to different portions of text based on whether they are hypothetical or factual, a third category of weight may be applied to portions of text that are considered indeterminate, i.e. neither confirmed to be hypothetical or factual.

Thus, in this way, the identification of ignore sub-trees may be personalized such that the personalized writing style and ignore triggers used by the source are considered when determining if a candidate or potential ignore sub-tree is an actual ignore sub-tree. As a result, different sources may have different terms/phrases identified as actual ignore triggers such that the operation of the hypothetical span analyzer 344 is customized to the particular source.

Figure 5:
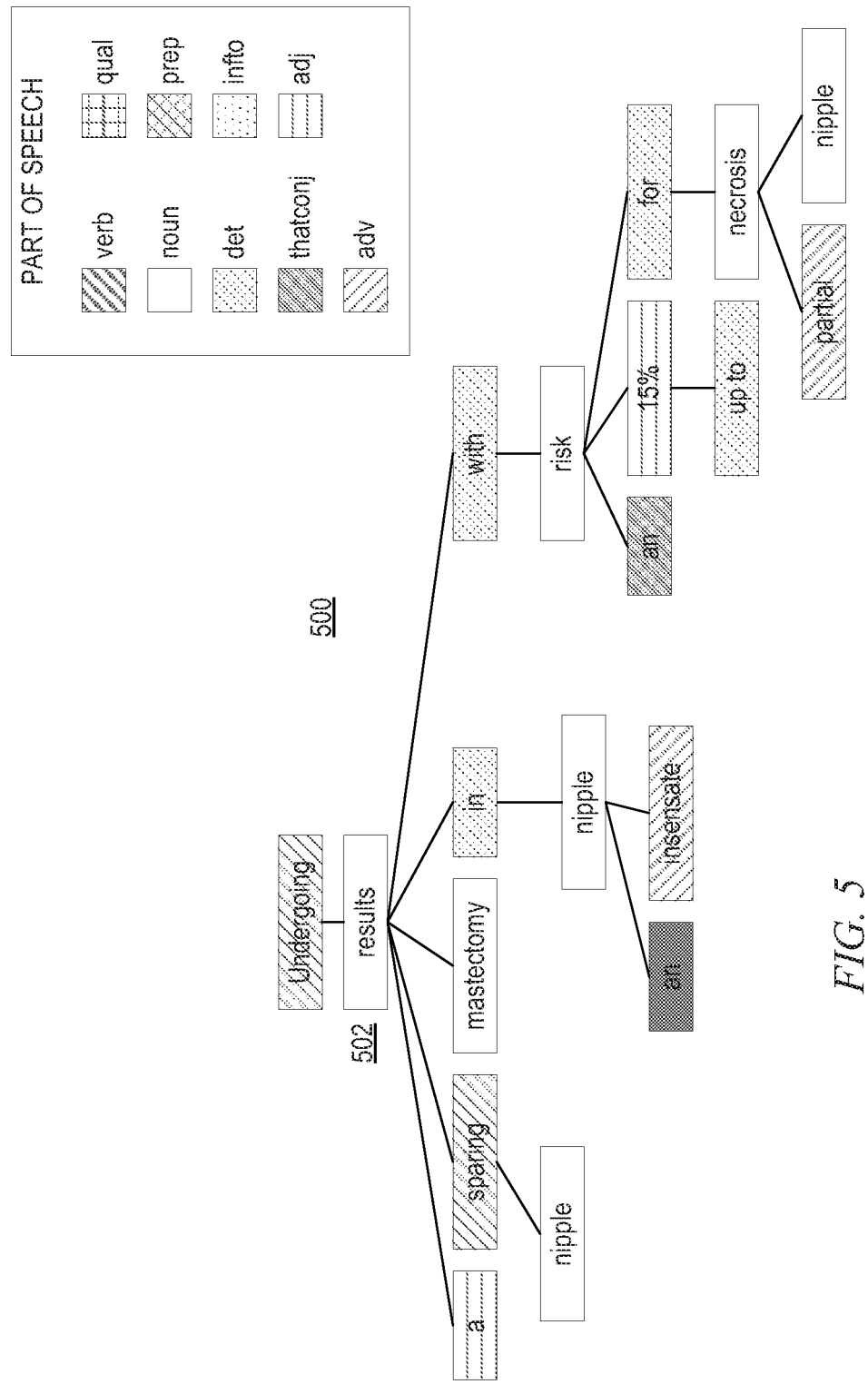
FIG. 5 is an example of another parse tree data structure for a sentence in which disambiguation of the node corresponding to an ignore trigger is performed in accordance with one illustrative embodiment.

FIG. 5 is an example of another parse tree data structure for a sentence in which disambiguation of the node corresponding to an ignore trigger is performed in accordance with one illustrative embodiment. As shown in FIG. 5, the parse tree 500 corresponds to the statement "Undergoing a nipple-sparing mastectomy results in an insensate nipple with an up to 15% risk of partial nipple necrosis." When one views the parse tree 500 of this sentence, it can be seen that the term "results in" is a phrase that captures all the tokens that are potentially a hypothetical span and this is generalizable enough not to cause any wrong annotations in other cases.

Comparing each token of each node in the parse tree 500 to ignore triggers in the hypothetical dictionary data structures 347, the node 502 is correctly identified as matching an ignore trigger but the token is associated with the "noun" part of speech in this example. Therefore, disambiguation of the token corresponding to node 502 is performed based on dictionary information, tense information, n-grams, ontological information, and the like. The disambiguation attempts to match the features of the token of the node 502 to other parts of the sentence, i.e. other parts of the sub-tree of the node 502 to disambiguate the language use of the token. For example, the definition of the term(s) of the token may be compared with other portions of the sentence to determine if it matches the other parts of speech of the other portions of the sentence.

For example, taking the sub-tree of the node 502 the corresponding sentence is "A nipple-sparing mastectomy results in an insensate nipple." The corresponding dataset of tuples, or n-grams, with a corresponding tuple containing medical adjusted ontology illustrating the part of speech pattern of the above sentence is as follows:

<noun><verb><noun> (this is a straight sentence parse tuple)

where the medical adjusted ontology tuple is:

<noun-procedure><verb><noun-body-part> (this is the sentence parse tuple adjusted for the domain)

The tuples are obtained from the training set. The <noun-procedure> in the above tuple matches "nipple-sparing mastectomy" in the sentence, the <noun-body-part> matches "insensate nipple", and from the dataset of tuples, it is expected that the trigger is a verb not a noun (as XSG identifies it). Because the sentence matches the tuple, it is concluded that the trigger must indeed be a verb and not a noun, and it can be identified as a hypothetical statement.

The dictionary definition of the term "results" that may be utilized in this example to disambiguation the token of node 502 is as follows:

1. to spring, arise, or proceed as a consequence of actions, circumstances, premises, etc.; be the outcome.
2. To terminate or end in a specified manner or thing.

From analyzing this information, it can be determined that token "results" of node 502 is being used as a verb in the sentence and thus, is likely an ignore trigger referencing a hypothetical span of text. Hence, the sub-tree of node 502 will be identified as an ignore sub-tree and may be further analyzed with regard to confirm triggers as discussed above. That is, once the part of speech is identified, the definition is parsed for terms. Based on the set of sentence pattern matches, the definition can help to confirm that the "trigger" is indeed correct. For this example, one of the sentence pattern includes noun—outcomes or calculations. The definition of "result," includes the term outcome. A set of these patterns that has been denoted by a subject matter expert will help to confirm usage of terms that can be various parts of speech.

As another example, consider the sentence "A mastectomy performed had good results." The corresponding tuple or n-gram for this sentence is as follows:
<noun><verb><adjective><noun>
where the medical adjusted ontology tuple is:
<noun-procedure><verb-action-past-tense><noun-outcome/calculation>

The result of analyzing this tuple, dictionary definition, ontology information, etc., indicates that the use of the term "result" is a noun, making it not an ignore trigger match since it is not a verb. If this tuple is not used, the term "results" could be taken as an ignore trigger when it is actually a fact in this sentence. In this particular sentence the matching tuple is noun: mastectomy, verb: performed, verb-action-past-tense: had, and noun-outcome/calculation: good results. It is known from training set data that this tuple is associated with facts and not hypotheticals. Therefore, finding this sentence matches the tuple, the mechanisms of the illustrative embodiment identifies the term "results" as a confirm trigger rather than an ignore trigger.

In order to identify whether a sentence matches a particular tuple, in some illustrative embodiments, the mechanisms of the illustrative embodiments may score the tuples relative to the sentence. For each tuple pattern there is a maximum score for matching the tuple pattern including the domain specific tuple pattern, in this case the medical adjusted ontology tuple, such that when all parts of speech and equivalent ontology tuples are found within the hypothetical span or the natural language content that contains a hypothetical span the maximum score is associated for the tuple. Each matching item is given a weight in the pattern, with noun and verb having the highest weight and the subject having the next highest weight. The score for the tuple pattern is an aggregate of the weighted value for each matching portion of the tuple pattern and when this the score is higher than a threshold, it can be determined that the tuple pattern has been sufficient matched and the term should be treated as a trigger, e.g., a hypothetical or confirm trigger depending on whether the tuple is for confirm or hypothetical trigger identification.

For example, in the above tuple pattern, the weights for the various parts of speech may be as follows: <noun>(2) <verb>(6)<adjective>(1)<noun-procedure>(3), <verb-action past tense>(2)<noun-outcome/calculation>(4), which gives a maximum score of 18. A threshold for confirming a trigger is highly weighted towards the correct parts of speech and thus, an example threshold score could be determined to be 10 such that if a portion of text matches parts of the tuple pattern so as to generate a weighted score of 10 or greater, it is considered to be a trigger. If more than one of these tuple patterns are matched over their corresponding threshold values, then confirmation of the trigger can be performed based on the number of matches.

It should be appreciated that the above process for identifying ignore sub-trees and confirm sub-trees may be performed with regard to each portion of text within the medical text, e.g., each sentence, such that the entirety of the medical text is analyzed to identify ignore (hypothetical) sub-trees and confirm (factual) sub-trees. The ignore sub-trees represent the hypothetical spans while the confirm sub-trees represent the factual spans. These hypothetical spans and factual spans may be provided to the medical text annotator 346 which generates the corresponding ignore (hypothetical) annotations and confirm (factual) annotations in the metadata 325 of the medical text, e.g., EMR 323, pointing to the corresponding hypothetical spans and factual spans in the medical text. The medical text, e.g., EMR 323, and the metadata 325 are returned to the healthcare cognitive system 300 for use in performing cognitive operations.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

Thus, the illustrative embodiments provide mechanisms for analyzing natural language content of a document, such as a medical text, to identify portions of text that reference hypothetical events, status, conditions, or the like and differentiate these hypotheticals from portions of text referencing actual facts. Corresponding annotations are provided for the various portions of text to identify them as hypothetical or factual based on the results of such analysis and these annotations are then provided to a cognitive system for use when performing its cognitive operations.

As noted above, in some illustrative embodiments, these cognitive operations may comprise a machine learning model performing machine learning, such as machine learning for determining appropriate medical treatment recommendations. For example, as part of a machine learning operation performed by a machine learning model, the patient EMRs for a plurality of patients may be retrieved from a patient registry of a corpus and used to draw correlations between patient attributes and corresponding prescribed treatments. For example, various medical maladies, patient attributes (e.g., age, gender, height, weight, particular lab results, etc.), and their corresponding treatments prescribed by medical personnel may be identified in the patient EMRs and used to generate a machine learning model of medical treatment recommendations. Such machine learning may correlate these medical maladies, patient attributes, and prescribed treatments, identify other corroborating evidence in the corpus or corpora, including other medical texts such as guidelines, positional papers, and the like, and generate a confidence in the treatment recommendation correlation.

In such an embodiment, the identification of hypothetical spans of text and annotation of such hypothetical spans of text, which corresponds to the ignore sub-trees identified by the mechanisms of the illustrative embodiments, may be used to ignore the hypothetical spans when performing the machine learning operations to learn the correlations of medical malady, patient attributes, and treatment. Thus, when the machine learning operation encounters a portion of text that is annotated as being a hypothetical span of text, that portion of text is ignored and not processed as part of the machine learning operation. In some illustrative embodiments, it may be determined that, while hypothetical in nature, the hypothetical span of text may still provide some insight into the validity of correlations of medical malady, patient attributes, and treatment and may instead of ignoring these portions of text, may give them relatively smaller weight during the evaluation than other portions of text that are determined to be associated with factual content. Thus, for example, when identifying evidential support for a correlation, hypothetical spans of text will provide relatively smaller amounts of evidential support for/against the correlation than other portions of text identified as being factual in nature.

Similarly, the cognitive operation may comprise the actual runtime determination of a treatment recommendation for a particular identified patient, such as described in the context of FIG. 3 above. In such a case, similar considerations of hypothetical spans of text may be performed by the healthcare cognitive system 300 when generating a treatment recommendation 328 to be returned to the user 306. That is, the hypothetical spans of text may be ignored or given relatively smaller weight, depending on the particular implementation, when evaluating the patient EMRs to determine appropriate treatments based on other evidential information in the corpora 322-326.

Hence, mechanisms are provided, in a data processing system having a processor and at least one memory, where the at least one memory has instructions which are executed by the processor and configure the processor to perform the operations corresponding to one or more of the illustrative embodiments described above. In one illustrative embodiment, these operations include: (1) receiving, by a data processing system, natural language content; (2) analyzing, by the data processing system, the natural language content to generate a parse tree data structure; (3) processing, by the data processing system, the parse tree data structure to identify one or more instances of candidate hypothetical spans in the natural language content, wherein hypothetical spans are terms or phrases indicative of a hypothetical statement; (4) calculating, by the data processing system, for each candidate hypothetical span, a confidence score value indicative of a confidence that the candidate hypothetical span is an actual hypothetical span based on a personalized hypothetical dictionary data structure associated with a source of the natural language content; and (5) performing, by the data processing system, an operation based on the natural language content. The operation is performed with portions of the natural language content corresponding to the one or more identified instances of actual hypothetical spans being given different relative weights within portions of the natural language content than other portions of the natural language content. In some illustrative embodiments, the operations may further include generating, by the data processing system, the personalized hypothetical dictionary data structure for the source of the natural language content based on analysis of writing style features utilized by the source of the natural language content.

In other illustrative embodiments the operations may include generating a set of actual hypothetical spans based on a comparison of confidence score values of the candidate hypothetical spans to at least one threshold value. Candidate hypothetical spans are added to the set of actual hypothetical spans in response to their corresponding confidence score values having a predetermined relationship to the at least one threshold value. Each source in a plurality of sources of natural language content has an associated personalized hypothetical dictionary data structure. At least two of the personalized hypothetical dictionary data structures have different hypothetical triggers determined based on analysis of the writing style features of the corresponding sources.

In still further illustrative embodiments, the personalized hypothetical dictionary data structure specifies one or more hypothetical triggers that are specific to the particular source associated with the personalized hypothetical dictionary data structure. In some cases, the one or more hypothetical triggers are identified through natural language processing of documents authored by the source to identify writing style features used by the source. In some implementations, the source is an institution and the writing style features include rules specified by the institution indication requirements of writing style to be used by authors when generating natural language content.

In some illustrative embodiments, the writing style features include both structural and content features of natural language content generated by the source and learned through machine learning algorithms applied to the natural language content generated by the source. In some illustrative embodiments, the writing style features of the source include patterns of language usage identified through statistical analysis of sentence style in natural language content generated by the source.

With some illustrative embodiments, processing the parse tree to identify one or more instances of hypothetical span includes identifying a hypothetical trigger within the parse tree data structure and annotating the natural language content signifying the content within the hypothetical span to be associated with the hypothetical trigger.

In still other illustrative embodiments, the operations may include removing, by the data processing system, one or more sub-tree data structures of the parse tree data structure that correspond to the one or more instances of actual hypothetical spans, to thereby generate a hypothetical pruned parse tree data structure, wherein the operation is performed based on the hypothetical pruned parse tree data structure. Other illustrative embodiments may include operations that include training, by the data processing system, a model of a natural language processing system based on the identification of the one or more instances of actual hypothetical spans in the natural language content, and performing, by the natural language processing system, natural language processing of natural language content based on the trained model.

In some illustrative embodiments, processing the parse tree data structure further includes, for each instance of a hypothetical trigger found in the parse tree data structure: (1) analyzing the hypothetical trigger using a dictionary data structure to determine a part-of-speech attribute of the hypothetical trigger; and (2) utilizing the determined part-of-speech attribute to determine a measure of whether or not the hypothetical trigger corresponds to a hypothetical statement. Utilizing the determined part-of-speech attribute to determine a measure of whether or not the hypothetical trigger corresponds to a hypothetical statement may include: (1) generating a tuple representation of a sub-tree data structure corresponding to the hypothetical trigger; (2) retrieving, from the dictionary data structure, one or more dictionary definitions of a term present in the hypothetical trigger; and (3) determining a part-of-speech attribute of the hypothetical trigger based on a correlation of the tuple representation of the sub-tree data structure with the one or more dictionary definitions. In some cases, in response to the part-of-speech attribute indicating that the hypothetical trigger is a noun, the sub-tree data structure corresponding to the hypothetical trigger is determined to not be directed to a hypothetical statement.

As noted above, in some illustrative embodiments, the natural language processing system is a medical treatment recommendation system, and the operation includes generating treatment recommendations based on content of a patient electronic medical record.

In some illustrative embodiments, processing the parse tree data structure further includes processing the parse tree data structure to identify instances of factual triggers, wherein factual triggers are terms or phrases indicative of a factual statement. Moreover, in some illustrative embodiments, operations are performed to determine if a factual sub-tree is present within a hypothetical sub-tree and, in response to the factual sub-tree being present within a hypothetical sub-tree, remove the factual sub-tree from the hypothetical sub-tree to generate a modified hypothetical sub-tree prior to further processing of the modified hypothetical sub-tree.

Figure 6A:
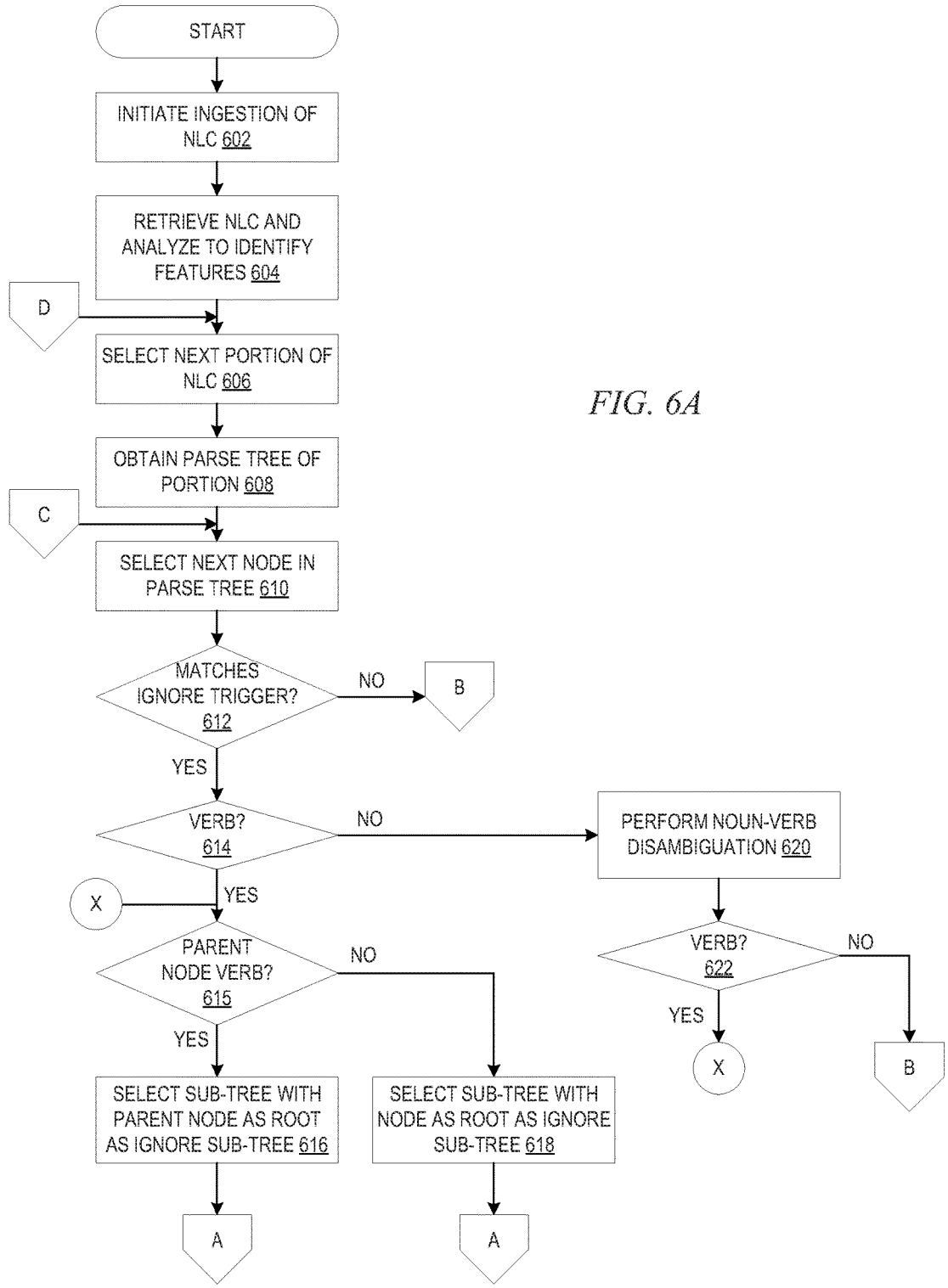
FIGS. 6A-6C illustrate a flowchart outlining an example operation of a medical text ingestion engine comprising a parse tree engine, hypothetical span analyzer, and medical text annotator in accordance with one illustrative embodiment.
Figure 6B:
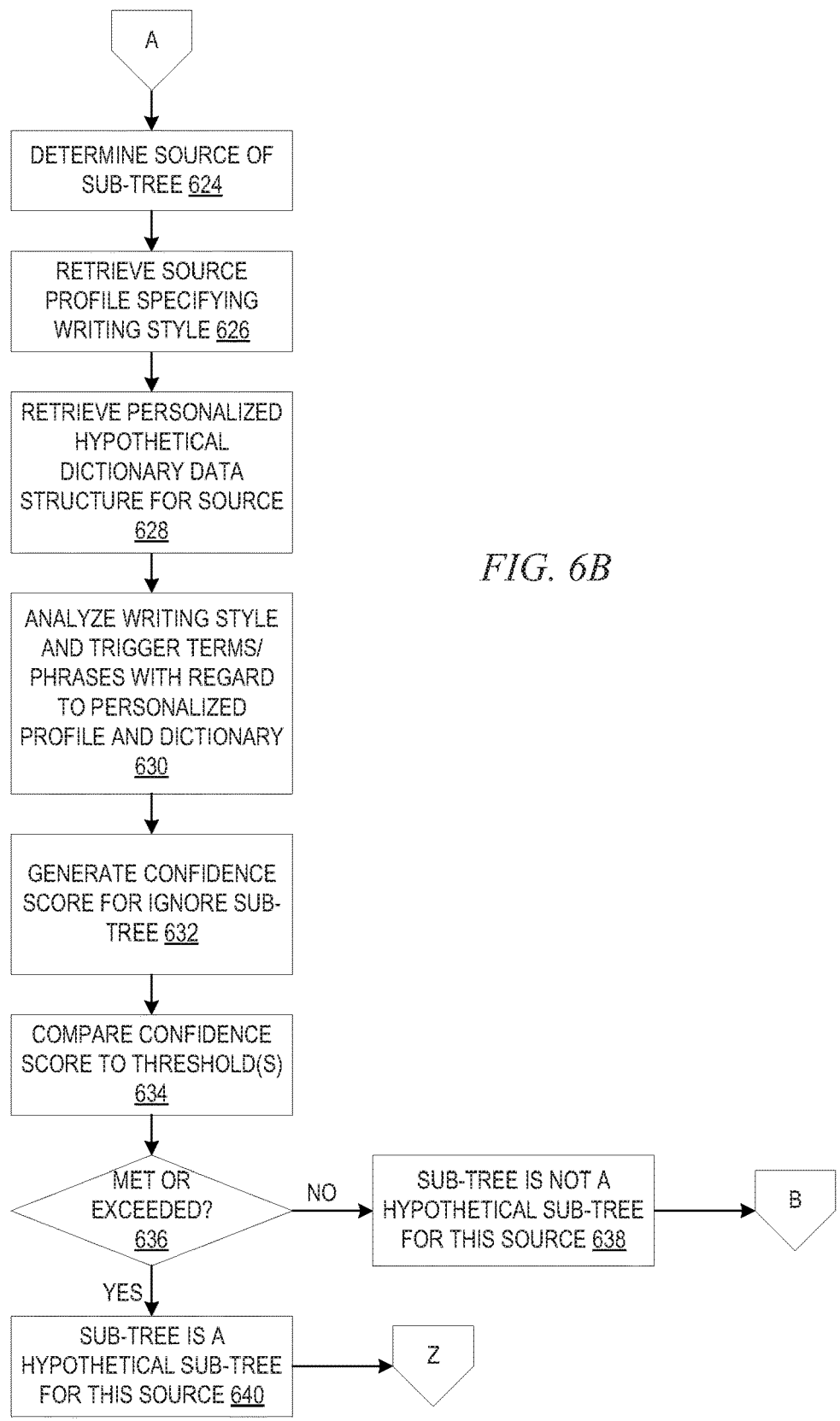
Figure 6C:
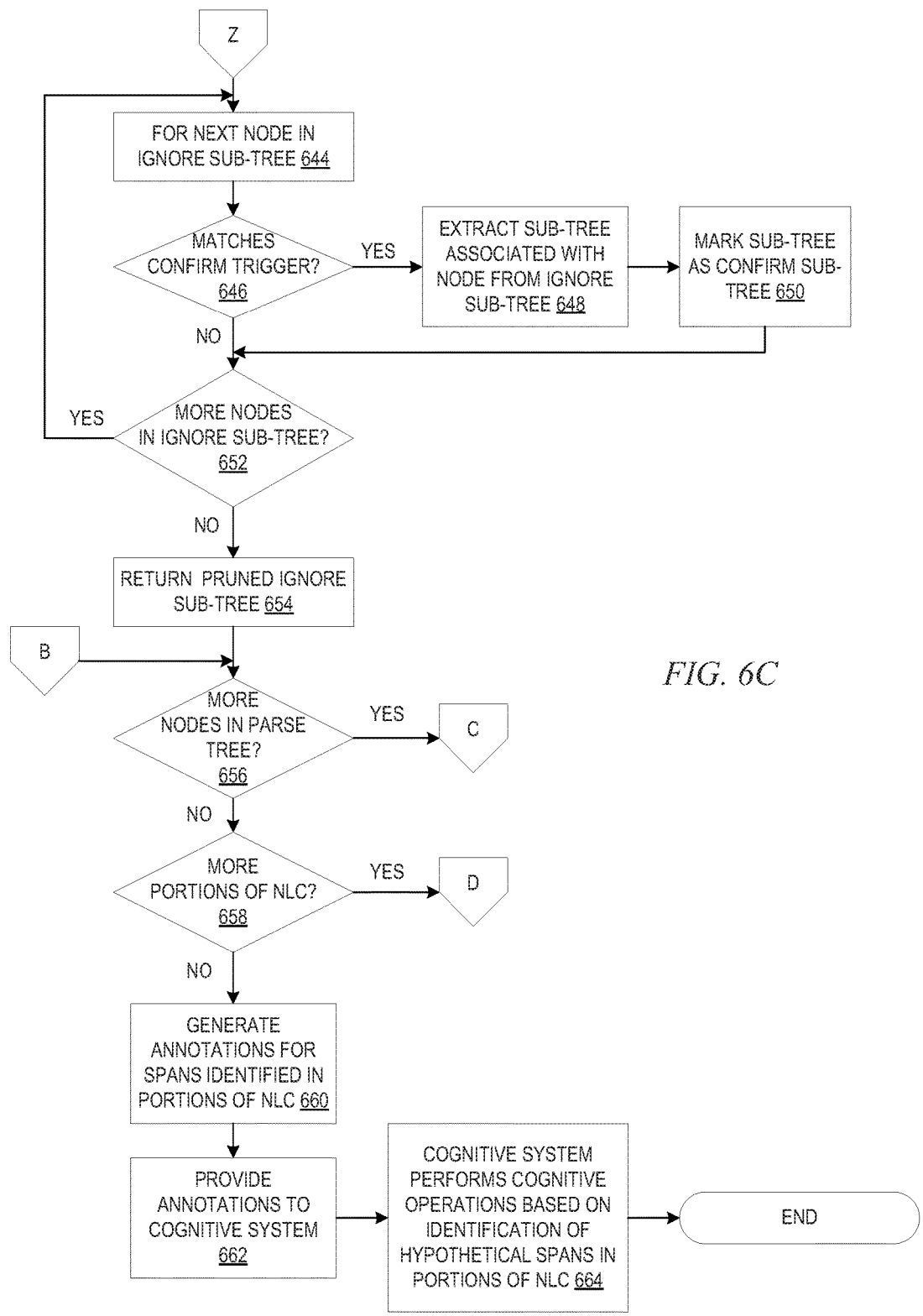

FIGS. 6A-6C illustrate a flowchart outlining an example operation of a medical text ingestion engine comprising a parse tree engine, hypothetical span analyzer, and medical text annotator in accordance with one illustrative embodiment. As shown in FIG. 6A, the operation starts with the initiation of ingestion of a natural language content (NLC), which may be a medical text, for example (step 602). The initiation of this ingestion may be in response to a request to perform a cognitive operation, as part of an initialization operation, as part of a machine learning operation, or the like. Natural language content is retrieved from a corpus and analyzed to identify various features of the portion of natural language content, e.g., parts of speech, tense of terms, ontological correlations between concepts, etc. (step 604). In some illustrative embodiments, this natural language content is a patient EMR which is being ingested by a healthcare cognitive system to perform a healthcare based cognitive operation. In still further illustrative embodiments, the healthcare based cognitive operation is one of a machine learning operation for configuring a machine learning model of a medical treatment recommendation cognitive system. In other illustrative embodiments, the healthcare based cognitive operation is a runtime medical treatment recommendation operation for generating a medical treatment recommendation for a specified patient as part of the processing of a request or input question submitted to the healthcare cognitive system.

A next portion of the natural language content is selected, e.g., a sentence, for hypothetical span analysis (step 606). A parse tree of the portion of natural language content is generated, such as by a parse tree engine of the medical text ingestion engine (step 608). For a next node in the parse tree (step 610), a determination is made as to whether the token corresponding to the node matches an ignore (hypothetical) trigger specified in a hypothetical dictionary data structure (step 612). If so, then the part of speech attribute of the token of the node is analyzed to determine if it is a verb (step 614). If so, then a determination is made as to whether the node's parent node is a verb (step 615). If so, then the sub-tree is selected, with the parent node being a root of the sub-tree, as an ignore sub-tree, or hypothetical sub-tree (step 616). If not, then the sub-tree is selected, with the node itself being the root of the sub-tree, as an ignore sub-tree, or hypothetical sub-tree (step 618). The operation then proceeds to step 624 in FIG. 6B.

If the token of the node is not a verb in step 614, then noun-verb disambiguation is performed (step 620) to determine if the token is being used as a noun or verb in the NLC. A determination is then made as to whether the disambiguation indicates that the token is a verb or a noun (step 622). If the token is a verb, the operation branches to step 614 where again the parent node is investigated and a corresponding sub-tree and root node are identified (steps 616 or 618). If the token is not a verb, then the operation branches to step 656 in FIG. 6C. The same is true if the node's token does not match an ignore trigger in step 612, i.e. the operation branches to step 656 in FIG. 6C.

With reference now to FIG. 6B, the operation outlined in FIG. 6B corresponds to the evaluation of the ignore sub-tree with regard to the specific source. That is, the operations shown in FIG. 6B further evaluate the candidate or potential ignore sub-tree identified in steps 616 or 618 to determine if, for the source of the text of the candidate or potential ignore sub-tree, that the evidence weighs in favor of the candidate ignore sub-tree being an actual ignore sub-tree. This evaluation takes into consideration the personal writing style, ignore trigger usage (word or term/phrase usage) and other personalized characteristics of the source's style of presenting information.

As shown in FIG. 6B, the source of the text corresponding to the candidate ignore sub-tree is determined (step 624). This may involve identifying the source from metadata associated with the text, identifying references to the source in the text itself, or any other mechanism by which the source of a portion of text may be identified. Having identified the source of the text of the candidate ignore sub-tree, a corresponding personalized profile specifying the writing style of the source is retrieved based on the identity of the source (step 626). Moreover, a personalized hypothetical dictionary data structure for the source may also be retrieved based on the identity of the source (step 628). The writing style and ignore trigger terms/phrases of the candidate ignore sub-tree text are compared to the personalized profile and hypothetical dictionary data structures to determine degrees of matching between features of the text of the candidate ignore sub-tree and writing style and ignore trigger (words/terms/phrases) usage specified in the personalized profile and hypothetical dictionary data structures (step 630).

Based on the determined degree of matching between the personalized profile and hypothetical dictionary data structures with the writing style and ignore trigger of the candidate ignore sub-tree, a confidence score is generated for the candidate ignore sub-tree (step 632). The confidence score is compared to a threshold confidence score value (step 634) and it is determined whether the threshold has been met or exceeded (step 636). If the threshold has not been met, then the candidate ignore sub-tree is not considered to be an actual ignore or hypothetical sub-tree for this particular source even though the initial analysis indicated the sub-tree to be associated with an ignore trigger (step 638). The operation then continues to step 656 in FIG. 6C. If the threshold has been met or exceeded, then the candidate ignore sub-tree is considered to be an actual ignore or hypothetical sub-tree for this source (step 640) and the operation continues to step 644 in FIG. 6C.

Referring now to FIG. 6C, the operation selects a next node in the ignore sub-tree (step 644) and determines if the token of that node matches a confirm trigger as specified by an entry in a factual dictionary data structure, for example (step 646). If the node's token does match a confirm trigger, then the sub-tree associated with that node is extracted from the ignore sub-tree (step 648) and marked as a confirm, or factual, sub-tree (step 650) corresponding to a factual span of text.

Thereafter, or if the node's token does not match a confirm trigger, a determination is made as to whether there are more nodes in the ignore sub-tree to be processed (step 652). If so, the operation returns to step 644 at which point the next node is selected. If not, the operation returns the pruned ignore sub-tree, i.e. the ignore sub-tree without the embedded confirm sub-trees (step 634). A determination is then made as to whether there are more nodes in the parse tree to be processed (step 656). If so, the operation returns to step 610 in FIG. 6A. If not, the operation determines whether there are more portions of the NLC to be processed (step 658). If so, the operation returns to step 606 in FIG. 6A. If not, the operation generates annotations for the hypothetical spans, corresponding to the ignore sub-trees, of the NLC and optionally the factual spans, corresponding to the confirm sub-trees, of the NLC (step 660). The annotations are provided to the cognitive system (step 662) and utilized to perform cognitive operations based on the identification of the hypothetical spans in the portions of NLC (step 664). The operation then terminates in the example flow but may be repeated for each portion of NLC ingested.

As noted above, the example illustrative embodiments set forth herein are presented in the context of a medical treatment recommendation system, which is but one example of a system that operates on natural language content to perform an algorithm operation, such as a cognitive operation which simulates human thought processes. The illustrative embodiments and the invention as a whole are not limited to such a domain and may be used with any domains of natural language content as will be readily apparent to those of ordinary skill in the art in view of the present disclosure. For example, judicial and law enforcement domains, financial analysis domains, governmental analysis domains, and the like, may all be used with the mechanisms of the illustrative embodiments.

Thus, looking back to FIG. 3, the various medical domain specific elements shown in FIG. 3 may be configured for different domains depending on the desired implementation. For example, the patient 302 may in fact be any source of information upon which a user operates to generate a request that is sent to the cognitive system 300, e.g., a personal record of some sort. Similarly, the medical text ingestion engine 340, medical text annotator 346, and various corpora 322-326 may be associated with the particular domain of the implementation or generalized to a text ingestion engine 340, text annotator 346, and corpora 322-326 such that the implementation is not domain specific. Moreover, the hypothetical dictionary 347 and factual dictionary 348 may implement text patterns for tuples specific to the particular domain of the implementation or may be more general in nature depending on the particular implementation desired. Essentially, the illustrative embodiments are not limited to any particular domain or implementation and may operate with any type of natural language content in which distinguishing factual spans from hypothetical spans is desirable for further processing or performance of operations on the natural language content.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions which are executed by the at least one processor and specifically configure the at least one processor to perform the method, wherein the method comprises:
   receiving, by the data processing system, natural language content;
   analyzing, by the data processing system, the natural language content to generate a parse tree data structure;
   processing, by the data processing system, the parse tree data structure to identify one or more instances of candidate hypothetical spans in the natural language content, wherein hypothetical spans are terms or phrases indicative of a hypothetical statement;
   calculating, by the data processing system, for each candidate hypothetical span, a confidence score value indicative of a confidence that the candidate hypothetical span is an actual hypothetical span based on a personalized hypothetical dictionary data structure associated with a source of the natural language content;
   generating, by the data processing system, one or more instances of actual hypothetical spans based on the confidence score values associated with the candidate hypothetical spans;
   removing, by the data processing system, one or more sub-tree data structures of the parse tree data structure that correspond to the one or more instances of actual hypothetical spans, to thereby generate a hypothetical pruned parse tree data structure; and
   performing, by the data processing system, an operation based on the natural language content, wherein the operation is performed with portions of the natural language content, corresponding to the one or more identified instances of actual hypothetical spans, being given different relative weights, than other portions of the natural language content that do not correspond to the one or more identified instances of actual hypothetical spans, and wherein the operation is performed based on the hypothetical pruned parse tree data structure.

2. The method of claim 1, further comprising:
   generating, by the data processing system, the personalized hypothetical dictionary data structure for the source of the natural language content based on analysis of writing style features utilized by the source of the natural language content.

3. The method of claim 1, wherein generating one or more instances of actual hypothetical spans comprises comparing the confidence score values of the candidate hypothetical spans to at least one threshold value, wherein candidate hypothetical spans are added to the one or more instances of actual hypothetical spans in response to their corresponding confidence score values having a predetermined relationship to the at least one threshold value.

4. The method of claim 1, wherein each source in a plurality of sources of natural language content has an associated personalized hypothetical dictionary data structure, and wherein at least two of the personalized hypothetical dictionary data structures have different hypothetical triggers determined based on analysis of the writing style features of the corresponding sources.

5. The method of claim 1, wherein the personalized hypothetical dictionary data structure specifies one or more hypothetical triggers that are specific to the particular source associated with the personalized hypothetical dictionary data structure.

6. The method of claim 5, wherein the one or more hypothetical triggers are identified through natural language processing of documents authored by the source to identify writing style features used by the source.

7. The method of claim 6, wherein the source is an institution, and wherein the writing style features comprise rules, specified by the institution, indicating requirements of writing style to be used by authors when generating natural language content.

8. The method of claim 2, wherein the writing style features comprise both structural and content features of natural language content generated by the source and learned through machine learning algorithms applied to the natural language content generated by the source.

9. The method of claim 2, wherein the writing style features of the source comprise patterns of language usage identified through statistical analysis of sentence style in natural language content generated by the source.

10. The method of claim 1, wherein processing the parse tree data structure to identify one or more instances of candidate hypothetical span comprises:
    identifying a hypothetical trigger within the parse tree data structure; and
    annotating the natural language content signifying the content within the hypothetical span to be associated with the hypothetical trigger.

11. The method of claim 1, wherein the performing the operation comprises:
    training, by the data processing system, a model of a natural language processing system based on the generated one or more instances of actual hypothetical spans in the natural language content; and
    performing, by the natural language processing system, natural language processing of natural language content based on the trained model.

12. The method of claim 10, wherein processing the parse tree data structure further comprises, for each instance of a hypothetical trigger found in the parse tree data structure:
    analyzing the hypothetical trigger using a dictionary data structure to determine a part-of-speech attribute of the hypothetical trigger; and
    utilizing the determined part-of-speech attribute to determine a measure of whether or not the hypothetical trigger corresponds to a hypothetical statement.

13. The method of claim 12, wherein utilizing the determined part-of-speech attribute to determine a measure of whether or not the hypothetical trigger corresponds to a hypothetical statement comprises:
    generating a tuple representation of a sub-tree data structure corresponding to the hypothetical trigger;
    retrieving, from the dictionary data structure, one or more dictionary definitions of a term present in the hypothetical trigger; and determining a part-of-speech attribute of the hypothetical trigger based on a correlation of the tuple representation of the sub-tree data structure with the one or more dictionary definitions.

14. The method of claim 13, wherein, in response to the part-of-speech attribute indicating that the hypothetical trigger is a noun, the sub-tree data structure corresponding to the hypothetical trigger is determined to not be directed to a hypothetical statement.

15. The method of claim 1, wherein the data processing system comprises a medical treatment recommendation system, and wherein the operation comprises generating, by the medical treatment recommendation system, treatment recommendations based on content of a patient electronic medical record.

16. The method of claim 1, wherein processing the parse tree data structure further comprises processing the parse tree data structure to identify instances of factual triggers, wherein factual triggers are terms or phrases indicative of a factual statement.

17. The method of claim 16, further comprising:
determining if a factual sub-tree is present within a hypothetical sub-tree; and
in response to the factual sub-tree being present within a hypothetical sub-tree, removing the factual sub-tree from the hypothetical sub-tree to generate a modified hypothetical sub-tree prior to further processing of the modified hypothetical sub-tree.

18. A computer program product comprising a non-transitory computer readable medium having a computer readable program stored therein, wherein the computer readable program, when executed on a computing device, specifically configures the computing device, and causes the computing device, to:
receive natural language content;
analyze the natural language content to generate a parse tree data structure;
process the parse tree data structure to identify one or more instances of candidate hypothetical spans in the natural language content, wherein hypothetical spans are terms or phrases indicative of a hypothetical statement;
calculate, for each candidate hypothetical span, a confidence score value indicative of a confidence that the candidate hypothetical span is an actual hypothetical span based on a personalized hypothetical dictionary data structure associated with a source of the natural language content;
generate one or more instances of actual hypothetical spans based on the confidence score values associated with the candidate hypothetical spans;
remove one or more sub-tree data structures of the parse tree data structure that correspond to the one or more instances of actual hypothetical spans, to thereby generate a hypothetical pruned parse tree data structure; and
perform an operation based on the natural language content, wherein the operation is performed with portions of the natural language content corresponding to the one or more identified instances of actual hypothetical spans being given different relative weights, than other portions of the natural language content that do not correspond to the one or more identified instances of actual hypothetical spans, and wherein the operation is performed based on the hypothetical pruned parse tree data structure.

19. An apparatus comprising:
a processor; and
a memory coupled to the processor, wherein the memory comprises instructions which, when executed by the processor, specifically configures the processor and causes the processor to:
receive natural language content;
analyze the natural language content to generate a parse tree data structure;
process the parse tree data structure to identify one or more instances of candidate hypothetical spans in the natural language content, wherein hypothetical spans are terms or phrases indicative of a hypothetical statement;
calculate, for each candidate hypothetical span, a confidence score value indicative of a confidence that the candidate hypothetical span is an actual hypothetical span based on a personalized hypothetical dictionary data structure associated with a source of the natural language content;
generate one or more instances of actual hypothetical spans based on the confidence score values associated with the candidate hypothetical spans;
remove one or more sub-tree data structures of the parse tree data structure that correspond to the one or more instances of actual hypothetical spans, to thereby generate a hypothetical pruned parse tree data structure; and
perform an operation based on the natural language content, wherein the operation is performed with portions of the natural language content corresponding to the one or more identified instances of actual hypothetical spans being given different relative weights, than other portions of the natural language content that do not correspond to the one or more identified instances of actual hypothetical spans, and wherein the operation is performed based on the hypothetical pruned parse tree data structure.

* * * * *